(12) United States Patent
Boesen

(10) Patent No.: US 11,694,771 B2
(45) Date of Patent: Jul. 4, 2023

(54) SYSTEM AND METHOD FOR POPULATING ELECTRONIC HEALTH RECORDS WITH WIRELESS EARPIECES

(71) Applicant: BRAGI GmbH, Munich (DE)

(72) Inventor: Peter Vincent Boesen, Munich (DE)

(73) Assignee: BRAGI GMBH, Munich (DE)

( * ) Notice: Subject to any disclaimer, the term of this patent is extended or adjusted under 35 U.S.C. 154(b) by 198 days.

(21) Appl. No.: 15/927,851

(22) Filed: Mar. 21, 2018

(65) Prior Publication Data

US 2018/0277238 A1 Sep. 27, 2018

Related U.S. Application Data

(60) Provisional application No. 62/475,052, filed on Mar. 22, 2017.

(51) Int. Cl.
*G16H 10/20* (2018.01)
*G16H 10/60* (2018.01)
*A61B 5/00* (2006.01)
*A61B 5/01* (2006.01)
*A61B 5/0205* (2006.01)
(Continued)

(52) U.S. Cl.
CPC .......... *G16H 10/20* (2018.01); *A61B 5/0024* (2013.01); *A61B 5/01* (2013.01); *A61B 5/0205* (2013.01); *A61B 5/6817* (2013.01); *G16H 10/60* (2018.01); *G16H 80/00* (2018.01); *H04R 1/1041* (2013.01); *A61B 5/021* (2013.01); *A61B 5/02438* (2013.01); *A61B 2562/0219* (2013.01); *H04R 1/1016* (2013.01); *H04R 2420/07* (2013.01)

(58) Field of Classification Search
CPC ......... G06Q 50/24; G16H 10/00–80/00; G06F 19/32–36
USPC ....................................................... 705/2–3
See application file for complete search history.

(56) References Cited

U.S. PATENT DOCUMENTS 2,325,590 A 8/1943 Carlisle et al.
2,430,229 A 11/1947 Kelsey
(Continued)

FOREIGN PATENT DOCUMENTS

CN 204244472 U 4/2015
CN 104683519 A 6/2015
(Continued)

OTHER PUBLICATIONS

Screen captures from YouTube video clip entitled "Nuance Healthcare Florence Workflow Concept with Samsung Smartwatch Demo English," 13 pages, uploaded on Jul. 3, 2015 by user "Nuance Deutschland". Retrieved from Internet: <https://www.youtube.com/watch?v=I-NVD60oyn0>.*

(Continued)

*Primary Examiner* — Lena Najarian
(74) *Attorney, Agent, or Firm* — Goodhue, Coleman & Owens, P.C.

(57) ABSTRACT

A system, method and wireless earpieces for populating an electronic health record utilizing wireless earpieces. Sensor measurements of a user are performed utilizing sensors of the wireless earpieces. The sensor measurements are analyzed. The sensor measurements are associated with the electronic health record of the user. The electronic health record of the user is populated with the sensor measurements. Communications including information from the electronic health record are communicated.

13 Claims, 7 Drawing Sheets

(51) Int. Cl.
  *H04R 1/10* (2006.01)
  *G16H 80/00* (2018.01)
  *A61B 5/021* (2006.01)
  *A61B 5/024* (2006.01)

(56) References Cited

U.S. PATENT DOCUMENTS

| | | | |
|---|---|---|---|
| 3,047,089 | A | 7/1962 | Zwislocki |
| D208,784 | S | 10/1967 | Sanzone |
| 3,586,794 | A | 6/1971 | Michaelis |
| 3,696,377 | A | 10/1972 | Wall |
| 3,934,100 | A | 1/1976 | Harada |
| 3,983,336 | A | 9/1976 | Malek et al. |
| 4,069,400 | A | 1/1978 | Johanson et al. |
| 4,150,262 | A | 4/1979 | Ono |
| 4,334,315 | A | 6/1982 | Ono et al. |
| D266,271 | S | 9/1982 | Johanson et al. |
| 4,375,016 | A | 2/1983 | Harada |
| 4,588,867 | A | 5/1986 | Konomi |
| 4,617,429 | A | 10/1986 | Bellafiore |
| 4,654,883 | A | 3/1987 | Iwata |
| 4,682,180 | A | 7/1987 | Gans |
| 4,791,673 | A | 12/1988 | Schreiber |
| 4,852,177 | A | 7/1989 | Ambrose |
| 4,865,044 | A | 9/1989 | Wallace et al. |
| 4,984,277 | A | 1/1991 | Bisgaard et al. |
| 5,008,943 | A | 4/1991 | Arndt et al. |
| 5,185,802 | A | 2/1993 | Stanton |
| 5,191,602 | A | 3/1993 | Regen et al. |
| 5,201,007 | A | 4/1993 | Ward et al. |
| 5,201,008 | A | 4/1993 | Arndt et al. |
| D340,286 | S | 10/1993 | Seo |
| 5,280,524 | A | 1/1994 | Norris |
| 5,295,193 | A | 3/1994 | Ono |
| 5,298,692 | A | 3/1994 | Ikeda et al. |
| 5,343,532 | A | 8/1994 | Shugart |
| 5,347,584 | A | 9/1994 | Narisawa |
| 5,363,444 | A | 11/1994 | Norris |
| 5,444,786 | A | 8/1995 | Raviv |
| D367,113 | S | 2/1996 | Weeks |
| 5,497,339 | A | 3/1996 | Bernard |
| 5,606,621 | A | 2/1997 | Reiter et al. |
| 5,613,222 | A | 3/1997 | Guenther |
| 5,654,530 | A | 8/1997 | Sauer et al. |
| 5,692,059 | A | 11/1997 | Kruger |
| 5,721,783 | A | 2/1998 | Anderson |
| 5,748,743 | A | 5/1998 | Weeks |
| 5,749,072 | A | 5/1998 | Mazurkiewicz et al. |
| 5,771,438 | A | 6/1998 | Palermo et al. |
| D397,796 | S | 9/1998 | Yabe et al. |
| 5,802,167 | A | 9/1998 | Hong |
| 5,844,996 | A | 12/1998 | Enzmann et al. |
| D410,008 | S | 5/1999 | Almqvist |
| 5,929,774 | A | 7/1999 | Charlton |
| 5,933,506 | A | 8/1999 | Aoki et al. |
| 5,949,896 | A | 9/1999 | Nageno et al. |
| 5,987,146 | A | 11/1999 | Pluvinage et al. |
| 6,021,207 | A | 2/2000 | Puthuff et al. |
| 6,054,989 | A | 4/2000 | Robertson et al. |
| 6,081,724 | A | 6/2000 | Wilson |
| 6,084,526 | A | 7/2000 | Blotky et al. |
| 6,094,492 | A | 7/2000 | Boesen |
| 6,111,569 | A | 8/2000 | Brusky et al. |
| 6,112,103 | A | 8/2000 | Puthuff |
| 6,157,727 | A | 12/2000 | Rueda |
| 6,167,039 | A | 12/2000 | Karlsson et al. |
| 6,181,801 | B1 | 1/2001 | Puthuff et al. |
| 6,185,152 | B1 | 2/2001 | Shen |
| 6,208,372 | B1 | 3/2001 | Barraclough |
| 6,230,029 | B1 | 5/2001 | Yegiazaryan et al. |
| 6,275,789 | B1 | 8/2001 | Moser et al. |
| 6,339,754 | B1 | 1/2002 | Flanagan et al. |
| D455,835 | S | 4/2002 | Anderson et al. |
| 6,408,081 | B1 | 6/2002 | Boesen |
| 6,424,820 | B1 | 7/2002 | Burdick et al. |
| D464,039 | S | 10/2002 | Boesen |
| 6,470,893 | B1 | 10/2002 | Boesen |
| D468,299 | S | 1/2003 | Boesen |
| D468,300 | S | 1/2003 | Boesen |
| 6,542,721 | B2 | 4/2003 | Boesen |
| 6,560,468 | B1 | 5/2003 | Boesen |
| 6,563,301 | B2 | 5/2003 | Gventer |
| 6,654,721 | B2 | 11/2003 | Handelman |
| 6,664,713 | B2 | 12/2003 | Boesen |
| 6,690,807 | B1 | 2/2004 | Meyer |
| 6,694,180 | B1 | 2/2004 | Boesen |
| 6,718,043 | B1 | 4/2004 | Boesen |
| 6,738,485 | B1 | 5/2004 | Boesen |
| 6,748,095 | B1 | 6/2004 | Goss |
| 6,754,358 | B1 | 6/2004 | Boesen et al. |
| 6,784,873 | B1 | 8/2004 | Boesen et al. |
| 6,823,195 | B1 | 11/2004 | Boesen |
| 6,852,084 | B1 | 2/2005 | Boesen |
| 6,879,698 | B2 | 4/2005 | Boesen |
| 6,892,082 | B2 | 5/2005 | Boesen |
| 6,920,229 | B2 | 7/2005 | Boesen |
| 6,952,483 | B2 | 10/2005 | Boesen et al. |
| 6,987,986 | B2 | 1/2006 | Boesen |
| 7,010,137 | B1 | 3/2006 | Leedom et al. |
| 7,113,611 | B2 | 9/2006 | Leedom et al. |
| D532,520 | S | 11/2006 | Kampmeier et al. |
| 7,136,282 | B1 | 11/2006 | Rebeske |
| 7,203,331 | B2 | 4/2007 | Boesen |
| 7,209,569 | B2 | 4/2007 | Boesen |
| 7,215,790 | B2 | 5/2007 | Boesen et al. |
| D549,222 | S | 8/2007 | Huang |
| D554,756 | S | 11/2007 | Sjursen et al. |
| 7,403,629 | B1 | 7/2008 | Aceti et al. |
| D579,006 | S | 10/2008 | Kim et al. |
| 7,463,902 | B2 | 12/2008 | Boesen |
| 7,508,411 | B2 | 3/2009 | Boesen |
| 7,532,901 | B1 | 5/2009 | LaFranchise et al. |
| D601,134 | S | 9/2009 | Elabidi et al. |
| 7,825,626 | B2 | 11/2010 | Kozisek |
| 7,859,469 | B1 | 12/2010 | Rosener et al. |
| 7,965,855 | B1 | 6/2011 | Ham |
| 7,979,035 | B2 | 7/2011 | Griffin et al. |
| 7,983,628 | B2 | 7/2011 | Boesen |
| D647,491 | S | 10/2011 | Chen et al. |
| 8,095,188 | B2 | 1/2012 | Shi |
| 8,108,143 | B1 | 1/2012 | Tester |
| 8,140,357 | B1 | 3/2012 | Boesen |
| 8,157,730 | B2 * | 4/2012 | LeBoeuf ............... G16H 50/30 600/300 |
| 8,251,875 | B2 * | 8/2012 | Ellis .................... A61B 5/1038 482/8 |
| D666,581 | S | 9/2012 | Perez |
| 8,300,864 | B2 | 10/2012 | Mullenborn et al. |
| 8,406,448 | B2 | 3/2013 | Lin |
| 8,430,817 | B1 | 4/2013 | Al-Ali et al. |
| 8,436,780 | B2 | 5/2013 | Schantz et al. |
| D687,021 | S | 7/2013 | Yuen |
| 8,679,012 | B1 | 3/2014 | Kayyali |
| 8,719,877 | B2 | 5/2014 | VonDoenhoff et al. |
| 8,774,434 | B2 | 7/2014 | Zhao et al. |
| 8,831,266 | B1 | 9/2014 | Huang |
| 8,891,800 | B1 | 11/2014 | Shaffer |
| 8,994,498 | B2 | 3/2015 | Agrafioti et al. |
| D728,107 | S | 4/2015 | Martin et al. |
| 9,013,145 | B2 | 4/2015 | Castillo et al. |
| 9,037,125 | B1 | 5/2015 | Kadous |
| D733,103 | S | 6/2015 | Jeong et al. |
| 9,081,944 | B2 | 7/2015 | Camacho et al. |
| 9,461,403 | B2 | 10/2016 | Gao et al. |
| 9,510,159 | B1 | 11/2016 | Cuddihy et al. |
| D773,439 | S | 12/2016 | Walker |
| D775,158 | S | 12/2016 | Dong et al. |
| D777,710 | S | 1/2017 | Palmborg et al. |
| 9,544,689 | B2 | 1/2017 | Fisher et al. |
| D788,079 | S | 5/2017 | Son et al. |
| 9,711,062 | B2 | 7/2017 | Ellis et al. |
| 9,729,979 | B2 | 8/2017 | Özden |
| 9,767,709 | B2 | 9/2017 | Ellis |
| 9,848,257 | B2 | 12/2017 | Ambrose et al. |

(56) References Cited

U.S. PATENT DOCUMENTS

| | | |
|---|---|---|
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Faenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0102931 A1 | 5/2004 | Ellis et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0197063 A1 | 9/2005 | White |
| 2005/0212911 A1 | 9/2005 | Marvit et al. |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2007/0102009 A1 | 5/2007 | Wong et al. |
| 2007/0239225 A1 | 10/2007 | Saringer |
| 2007/0269785 A1 | 11/2007 | Yamanoi |
| 2008/0076972 A1 | 3/2008 | Dorogusker et al. |
| 2008/0090622 A1 | 4/2008 | Kim et al. |
| 2008/0102424 A1 | 5/2008 | Holljes |
| 2008/0146890 A1 | 6/2008 | LeBoeuf et al. |
| 2008/0146892 A1* | 6/2008 | LeBoeuf ............... A61B 5/415 600/300 |
| 2008/0187163 A1 | 8/2008 | Goldstein et al. |
| 2008/0215239 A1 | 9/2008 | Lee |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2008/0298606 A1 | 12/2008 | Johnson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0047645 A1* | 2/2009 | Dibenedetto ......... G16H 15/00 434/258 |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0226017 A1 | 9/2009 | Abolfathi et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2009/0303073 A1 | 12/2009 | Gilling et al. |
| 2009/0304210 A1 | 12/2009 | Weisman |
| 2010/0033313 A1 | 2/2010 | Keady et al. |
| 2010/0166206 A1 | 7/2010 | Macours |
| 2010/0203831 A1 | 8/2010 | Muth |
| 2010/0210212 A1 | 8/2010 | Sato |
| 2010/0290636 A1 | 11/2010 | Mao et al. |
| 2010/0320961 A1 | 12/2010 | Castillo et al. |
| 2011/0018731 A1 | 1/2011 | Linsky et al. |
| 2011/0046983 A1* | 2/2011 | Soble ..................... G06Q 10/10 705/3 |
| 2011/0103609 A1 | 5/2011 | Pelland et al. |
| 2011/0137141 A1 | 6/2011 | Razoumov et al. |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2011/0293105 A1 | 12/2011 | Arie et al. |
| 2012/0057740 A1 | 3/2012 | Rosal |
| 2012/0155670 A1 | 6/2012 | Rutschman |
| 2012/0163626 A1 | 6/2012 | Booij et al. |
| 2012/0197737 A1 | 8/2012 | LeBoeuf et al. |
| 2012/0235883 A1 | 9/2012 | Border et al. |
| 2012/0309453 A1 | 12/2012 | Maguire |
| 2013/0106454 A1 | 5/2013 | Liu et al. |
| 2013/0154826 A1 | 6/2013 | Ratajczyk |
| 2013/0178967 A1 | 7/2013 | Mentz |
| 2013/0204617 A1 | 8/2013 | Kuo et al. |
| 2013/0293494 A1 | 11/2013 | Reshef |
| 2013/0316642 A1 | 11/2013 | Newham |
| 2013/0346168 A1 | 12/2013 | Zhou et al. |
| 2014/0004912 A1 | 1/2014 | Rajakarunanayake |
| 2014/0014697 A1 | 1/2014 | Schmierer et al. |
| 2014/0020089 A1 | 1/2014 | Perini, II |
| 2014/0072136 A1 | 3/2014 | Tenenbaum et al. |
| 2014/0072146 A1 | 3/2014 | Itkin et al. |
| 2014/0073429 A1 | 3/2014 | Meneses et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0146973 A1 | 5/2014 | Liu et al. |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0276227 A1 | 9/2014 | Pérez |
| 2014/0310595 A1 | 10/2014 | Acharya et al. |
| 2014/0321682 A1 | 10/2014 | Kofod-Hansen et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0056584 A1 | 2/2015 | Boulware et al. |
| 2015/0110587 A1 | 4/2015 | Hori |
| 2015/0148989 A1 | 5/2015 | Cooper et al. |
| 2015/0181356 A1 | 6/2015 | Krystek et al. |
| 2015/0230022 A1 | 8/2015 | Sakai et al. |
| 2015/0245127 A1 | 8/2015 | Shaffer |
| 2015/0256949 A1 | 9/2015 | Vanpoucke et al. |
| 2015/0264472 A1 | 9/2015 | Aase |
| 2015/0264501 A1 | 9/2015 | Hu et al. |
| 2015/0317565 A1 | 11/2015 | Li et al. |
| 2015/0358751 A1 | 12/2015 | Deng et al. |
| 2015/0359436 A1 | 12/2015 | Shim et al. |
| 2015/0364058 A1 | 12/2015 | Lagree et al. |
| 2015/0373467 A1 | 12/2015 | Gelter |
| 2015/0373474 A1 | 12/2015 | Kraft et al. |
| 2016/0033280 A1 | 2/2016 | Moore et al. |
| 2016/0034249 A1 | 2/2016 | Lee et al. |
| 2016/0051185 A1* | 2/2016 | Wisbey ............... A61B 5/02438 705/2 |
| 2016/0071526 A1 | 3/2016 | Wingate et al. |
| 2016/0072558 A1 | 3/2016 | Hirsch et al. |
| 2016/0073189 A1 | 3/2016 | Lindén et al. |
| 2016/0100262 A1 | 4/2016 | Inagaki |
| 2016/0119737 A1 | 4/2016 | Mehnert et al. |
| 2016/0124707 A1 | 5/2016 | Ermilov et al. |
| 2016/0125892 A1 | 5/2016 | Bowen et al. |
| 2016/0140870 A1 | 5/2016 | Connor |
| 2016/0142818 A1 | 5/2016 | Park |

(56) References Cited

U.S. PATENT DOCUMENTS

| | | |
|---|---|---|
| 2016/0162259 A1 | 6/2016 | Zhao et al. |
| 2016/0209691 A1 | 7/2016 | Yang et al. |
| 2016/0253994 A1 | 9/2016 | Panchapagesan et al. |
| 2016/0324478 A1 | 11/2016 | Goldstein |
| 2016/0330552 A1* | 11/2016 | Flood .................. H01Q 1/273 |
| 2016/0353196 A1 | 12/2016 | Baker et al. |
| 2016/0360350 A1 | 12/2016 | Watson et al. |
| 2016/0361020 A1* | 12/2016 | LeBoeuf ................ G16H 20/17 |
| 2017/0021257 A1 | 1/2017 | Gilbert et al. |
| 2017/0046503 A1 | 2/2017 | Cho et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0061817 A1 | 3/2017 | Mettler May |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0071546 A1* | 3/2017 | Jain ...................... A61B 5/0006 |
| 2017/0075654 A1* | 3/2017 | Shin ...................... G06F 3/167 |
| 2017/0078780 A1 | 3/2017 | Qian et al. |
| 2017/0078785 A1 | 3/2017 | Qian et al. |
| 2017/0100277 A1 | 4/2017 | Ke |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0112671 A1* | 4/2017 | Goldstein ............ H04R 25/554 |
| 2017/0127168 A1 | 5/2017 | Briggs et al. |
| 2017/0131094 A1 | 5/2017 | Kulik |
| 2017/0142511 A1 | 5/2017 | Dennis |
| 2017/0146801 A1 | 5/2017 | Stempora |
| 2017/0150920 A1 | 6/2017 | Chang et al. |
| 2017/0151085 A1 | 6/2017 | Chang et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0164890 A1 | 6/2017 | Leip et al. |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0251933 A1 | 9/2017 | Braun et al. |
| 2017/0257698 A1 | 9/2017 | Boesen et al. |
| 2017/0258329 A1 | 9/2017 | Marsh |
| 2017/0263236 A1 | 9/2017 | Boesen et al. |
| 2017/0263376 A1 | 9/2017 | Verschueren et al. |
| 2017/0266494 A1 | 9/2017 | Crankson et al. |
| 2017/0273622 A1 | 9/2017 | Boesen |
| 2017/0280257 A1 | 9/2017 | Gordon et al. |
| 2017/0301337 A1 | 10/2017 | Golani et al. |
| 2017/0361213 A1 | 12/2017 | Goslin et al. |
| 2017/0366233 A1 | 12/2017 | Hviid et al. |
| 2018/0007994 A1 | 1/2018 | Boesen et al. |
| 2018/0008194 A1 | 1/2018 | Boesen |
| 2018/0008198 A1 | 1/2018 | Kingscott |
| 2018/0009447 A1 | 1/2018 | Boesen et al. |
| 2018/0011006 A1 | 1/2018 | Kingscott |
| 2018/0011682 A1 | 1/2018 | Milevski et al. |
| 2018/0011994 A1 | 1/2018 | Boesen |
| 2018/0012228 A1 | 1/2018 | Milevski et al. |
| 2018/0013195 A1 | 1/2018 | Hviid et al. |
| 2018/0014102 A1 | 1/2018 | Hirsch et al. |
| 2018/0014103 A1 | 1/2018 | Martin et al. |
| 2018/0014104 A1 | 1/2018 | Boesen et al. |
| 2018/0014107 A1 | 1/2018 | Razouane et al. |
| 2018/0014108 A1 | 1/2018 | Dragicevic et al. |
| 2018/0014109 A1 | 1/2018 | Boesen |
| 2018/0014113 A1 | 1/2018 | Boesen |
| 2018/0014140 A1 | 1/2018 | Milevski et al. |
| 2018/0014436 A1 | 1/2018 | Milevski |
| 2018/0034951 A1 | 2/2018 | Boesen |
| 2018/0040093 A1 | 2/2018 | Boesen |
| 2018/0042501 A1 | 2/2018 | Adi et al. |

FOREIGN PATENT DOCUMENTS

| | | | |
|---|---|---|---|
| CN | 104837094 A | 8/2015 | |
| EP | 1017252 A2 | 7/2000 | |
| EP | 1469659 A1 | 10/2004 | |
| EP | 2903186 A1 | 8/2015 | |
| GB | 2074817 A | 11/1981 | |
| GB | 2508226 A | 5/2014 | |
| JP | 06292195 | 10/1994 | |
| JP | 5080558 B2 * | 11/2012 | ............. H03F 3/217 |
| WO | 2007034371 A2 | 3/2007 | |
| WO | 2008103925 A1 | 8/2008 | |
| WO | 2008113053 A1 | 9/2008 | |
| WO | 2011001433 A2 | 1/2011 | |
| WO | 2012071127 A1 | 5/2012 | |
| WO | 2013134956 A1 | 9/2013 | |
| WO | 2014043179 A2 | 3/2014 | |
| WO | 2014046602 A1 | 3/2014 | |
| WO | 2015061633 A2 | 4/2015 | |
| WO | 2015110577 A1 | 7/2015 | |
| WO | 2015110587 A1 | 7/2015 | |
| WO | 2016032990 A1 | 3/2016 | |
| WO | 2016187869 A1 | 12/2016 | |

OTHER PUBLICATIONS

Nelson, Rick. "Innovations Gather and Interpret EEG and Genetic Data." EE-Evaluation Engineering 54.1 (2015): 26(1). ProQuest. Web. Feb. 15, 2023. (Year: 2015).*

Alzahrani et al: "A Multi-Channel Opto-Electronic Sensor to Accurately Monitor Heart Rate against Motion Artefact during Exercise", Sensors, vol. 15, No. 10, Oct. 12, 2015, pp. 25681-25702, XPO55334602, DOI: 10.3390/s151025681 the whole document.

Announcing the $3,333,333 Stretch Goal (Feb. 24, 2014).

Ben Coxworth: "Graphene-based ink could enable low-cost, foldable electronics", "Journal of Physical Chemistry Letters", Northwestern University, (May 22, 2013).

Blain: "World's first graphene speaker already superior to Sennheiser MX400", htt://www.gizmag.com/graphene-speaker-beats-sennheiser-mx400/31660, (Apr. 15, 2014).

BMW, "BMW introduces BMW Connected—The personalized digital assistant", "http://bmwblog.com/2016/01/05/bmw-introduces-bmw-connected-the-personalized-digital-assistant", (Jan. 5, 2016).

BRAGI is on Facebook (2014).

BRAGI Update—Arrival of Prototype Chassis Parts—More People—Awesomeness (May 13, 2014).

BRAGI Update—Chinese New Year, Design Verification, Charging Case, More People, Timeline(Mar. 6, 2015).

BRAGI Update—First Sleeves From Prototype Tool—Software Development Kit (Jun. 5, 2014).

(56) References Cited

OTHER PUBLICATIONS

BRAGI Update—Let's Get Ready to Rumble, A Lot to be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From The First Month of Kickstarter—Update on Progress (Aug. 1, 2014).
BRAGI Update—Memories From The Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing—Oh Yeah, Timeline(Apr. 24, 2015).
BRAGI Update—The App Preview, The Charger, The SDK, BRAGI Funding and Chinese New Year (Feb. 11, 2015),
BRAGI Update—Years of Development, Moments of Utter Joy and Finishing What We Started(Jun. 5, 2015).
BRAGI Update—Alpha 5 and Back to China, Backer Day, On Track(May 16, 2015).
BRAGI Update—Beta2 Production and Factory Line(Aug. 20, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2015).
BRAGI Update—On Track, Design Verification, How It Works and What's Next(Jul. 15, 2015).
BRAGI Update—Status on Wireless, Supply, Timeline and Open House@BRAGI(Apr. 1, 2015)
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces A Health + Mobility Concept For Wellness In Mobility", Fountain Valley, Californa (2017).
International Search Report & Written Opinion, PCT/EP16/70245 (dated Nov. 16, 2016).
International Search Report & Written Opinion, PCT/EP2016/070231 (dated Nov. 18, 2016).
International Search Report & Written Opinion, PCT/EP2016/070247 (dated Nov. 18, 2016).
International Search Report & Written Opinion, PCT/EP2016/07216 (dated Oct. 18, 2016).
International Search Report and Written Opinion, PCT/EP2016/070228 (dated Jan. 9, 2017).
Jain A et al: "Score normalization in multimodal biometric systems", Pattern Recognition, Elsevier, GB, vol. 38, No. 12, Dec. 31, 2005, pp. 2270-2285, XPO27610849, ISSN: 0031-3203.
Last Push Before The Kickstarter Campaign Ends on Monday 4pm CET (Mar. 28, 2014).
Nemanja Paunovic et al, "A methodology for testing complex professional electronic systems", Serbian Journal of Electrical Engineering, vol. 9, No. 1, Feb. 1, 2012, pp. 71-80, XPO55317584, Yu.
Nigel Whitfield: "Fake tape detectors, 'from the stands' footie and UGH? Internet of Things in my set-top box" http://www.theregister.co.uk/2014/09/24/ibc_round_up_object_audio_dina_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometrics.html", 4 pages (Jul. 28, 2015).
Staab, Wayne J., et al., "A One-Size Disposable Hearing Aid is Introduced", The Hearing Journal 53(4):36-41) Apr. 2000. .
Stretchgoal—It's Your Dash (Feb. 14, 2014).
Stretchgoal—The Carrying Case for The Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Weisiger; "Conjugated Hyperbilirubinemia", Jan. 5, 2016.
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).
A. H. M. Akkermans, T. A. M. Kevenaarand D. W. E. Schobben, "Acoustic ear recognition for person identification," Published In: Fourth IEEE Workshop on Automatic Identification Advanced Technologies (AutoID'05), Buffalo, NY, USA, 2005, pp. 219-223.
BRAGI Update—What We Did Over Christmas, Las Vegas &CES (Jan. 19, 2015), pp. 1-21.
BRAGI Update—Certifications, Production, Ramping Up (Nov. 13, 2015), pp. 1-15.
BRAGI Update—On Track, On Track and Gems Overview (Jun. 24, 2015), pp. 1-19.

\* cited by examiner

SYSTEM AND METHOD FOR POPULATING ELECTRONIC HEALTH RECORDS WITH WIRELESS EARPIECES

PRIORITY STATEMENT

This application claims priority to 62/475,052 filed on Mar. 22, 2017 which is hereby incorporated by reference in its entirety.

FIELD OF THE INVENTION

The present invention relates to wireless earpieces. More specifically, but not exclusively, the present invention relates to generating electronic health records using biometric data from wireless earpieces.

BACKGROUND

One recognized use of wearable devices such as wireless earpieces is to provide biometric monitoring of a user in one form of another. However, the collection of such data by a set of wireless earpieces or other wearable devices may have limited utility. Such data may, in some cases, not be stored. Or if such data is stored, it may be stored only in a data silo. That is to say the data store for such data may be isolated and segregated from other data including other health data. Thus, data collected may be of limited utility. Another seemingly unrelated problem to one not having the benefit of this disclosure is that data from a biometric sensor may be of limited utility in diagnosing or monitoring an individual because it may lack sufficient context to be useful. What is a needed is a better way to use biometric data from wireless earpieces.

SUMMARY

Therefore, it is a primary object, feature, or advantage of the present invention to improve over the state of the art.

It is a further object, feature, or advantage of the present invention to provide an earpiece which can monitor the biometric sensors associated with the user.

A further object, feature, or advantage of the present invention is to correlate a particular user of the wireless earpiece with identifying information used to identify the user within an electronic health record.

A still further object, feature, or advantage of the present invention is to use environmental data or other data to assist in providing context for biometric data within an electronic health record.

Yet another object, feature, or advantage is to generate and/or populate electronic health records utilizing sensor readings from the wireless earpieces.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

According to one aspect, a system, method, and wireless earpieces are provided for populating an electronic health record utilizing wireless earpieces. The wireless earpieces may include a first earpiece and a second earpiece. The first earpiece may include a first earpiece housing, at least one biometric sensor disposed within the first earpiece housing, a wireless transceiver disposed within the first earpiece housing for voice communications, an intelligent control operatively connected to the at least one biometric sensor and the wireless radio transceiver, at least one microphone operatively connected to the intelligent control, an inertial sensor operatively connected to the intelligent control, a near field magnetic induction transceiver operatively connected to the intelligent control for communication with the second earpiece, a memory operatively connected to the intelligent control. The second earpiece may include a second earpiece housing, at least one biometric sensor disposed within the second earpiece housing, an intelligent control operatively connected to the at least one biometric sensor at least one microphone operatively connected to the intelligent control, an inertial sensor operatively connected to the intelligent control, a near field magnetic induction transceiver operatively connected to the intelligent control for communication with the second earpiece, and a memory operatively connected to the intelligent control. Sensor measurements of a user may be performed utilizing sensors of the wireless earpieces. The sensor measurements may be analyzed. The sensor measurements may then be associated with the electronic health record of the user such as by populating the electronic health record of the user with the sensor measurements.

According to another aspect, a wireless earpiece is provided. The wireless earpiece may include a frame for fitting in an ear of a user. The wireless earpiece may also include a logic engine controlling functionality of the wireless earpiece. The wireless earpiece may also include a number of sensors wherein there is at least one biometric sensor and at least one inertial sensor performing sensor measurements of the user. The wireless earpiece may include a memory for storing sensor data. The wireless earpiece may also include a transceiver communicating with at least a wireless device. The logic engine analyzes the sensor measurements and generates an electronic health record containing the sensor measurements. The sensor measurements may include biometric measurements and environmental measurements. The logic engine may generate a summary of the biometric measurements and the environmental measurements and include the summary within the electronic health record.

According to another aspect, a wireless earpiece is provided which may include a frame for fitting in an ear of a user. The wireless earpiece may also include a logic engine controlling functionality of the wireless earpiece. The wireless earpiece may also include a number of sensors wherein there is at least one biometric sensor and at least one inertial sensor performing sensor measurements of the user. The wireless earpiece may include a memory for storing sensor data. The wireless earpiece may also include a transceiver communicating with at least a wireless device. The logic engine analyzes the sensor measurements, associates the sensor measurements with the electronic health record of the user, populates the electronic health record of the user with the sensor measurements, and sends communications including the electronic health record.

According to another aspect, a method for populating an electronic health record using wireless earpieces is provided. The method includes performing a set of sensor measurements using one or more sensors of the wireless earpieces. The method further includes associating the sensor measurements with a user. The method further includes summarizing the set of sensor measurements using a processor of the wireless earpieces to provide a sensor data summary. The method further includes populating an electronic health record using the sensor measurements, the sensor data summary, and identifying information of the user. The identifying information of the user may include one or more of a patient id, a name of the user, a date of birth of the user, and a social security number of the user. The identifying information may include two or more of a patient id, a name of the user, a date of birth of the user, and a social security number of the user. The sensor data summary may include a time period for the sensor measurements, a high reading and a low reading for each type of sensor measurements, an average reading for a duration of the time period and/or other summarizations or abstracts of the sensor measurements. The one or more sensors may include at least one environmental sensor and at least one biometric sensor and the sensor measurements include both biometric data of the user from the at least one biometric sensor and environmental data of an environment associated with the user from the at least one environmental sensor. The environmental data may provide context for the biometric data. The biometric data may be of various types such as pulse data and inertial data.

According to another aspect, a method for populating an electronic health record utilizing wireless earpieces is provided. The method includes providing the wireless earpieces. The wireless earpieces are provided by making them available, selling them, obtaining them, or otherwise providing them. The method includes identifying a user of the wireless earpieces. This may be performed in various ways such as biometrically such as voice identification, receiving a password or pass phrase, or otherwise identifying the user of the wireless earpieces. It is contemplated, that a set of wireless earpieces may have only one user and in such cases identifying the wireless earpieces is sufficient to identify the user. The method further provides for performing sensor measurements of the user utilizing sensors of the wireless earpieces. The sensors may include at least one biometric sensor and at least one environmental sensor. The method may further include analyzing the sensor measurements to store in the electronic health record and generating a summary of the sensor measurements. The method may further include storing the sensor measurements in the memory of the wireless earpieces, associating the sensor measurements with the electronic health record of the user using biometric sensor measurements, populating the electronic health record of the user with the sensor measurements, and sending communications including information from the electronic health record from the wireless earpieces to another device.

DETAILED DESCRIPTION

Figure 1:
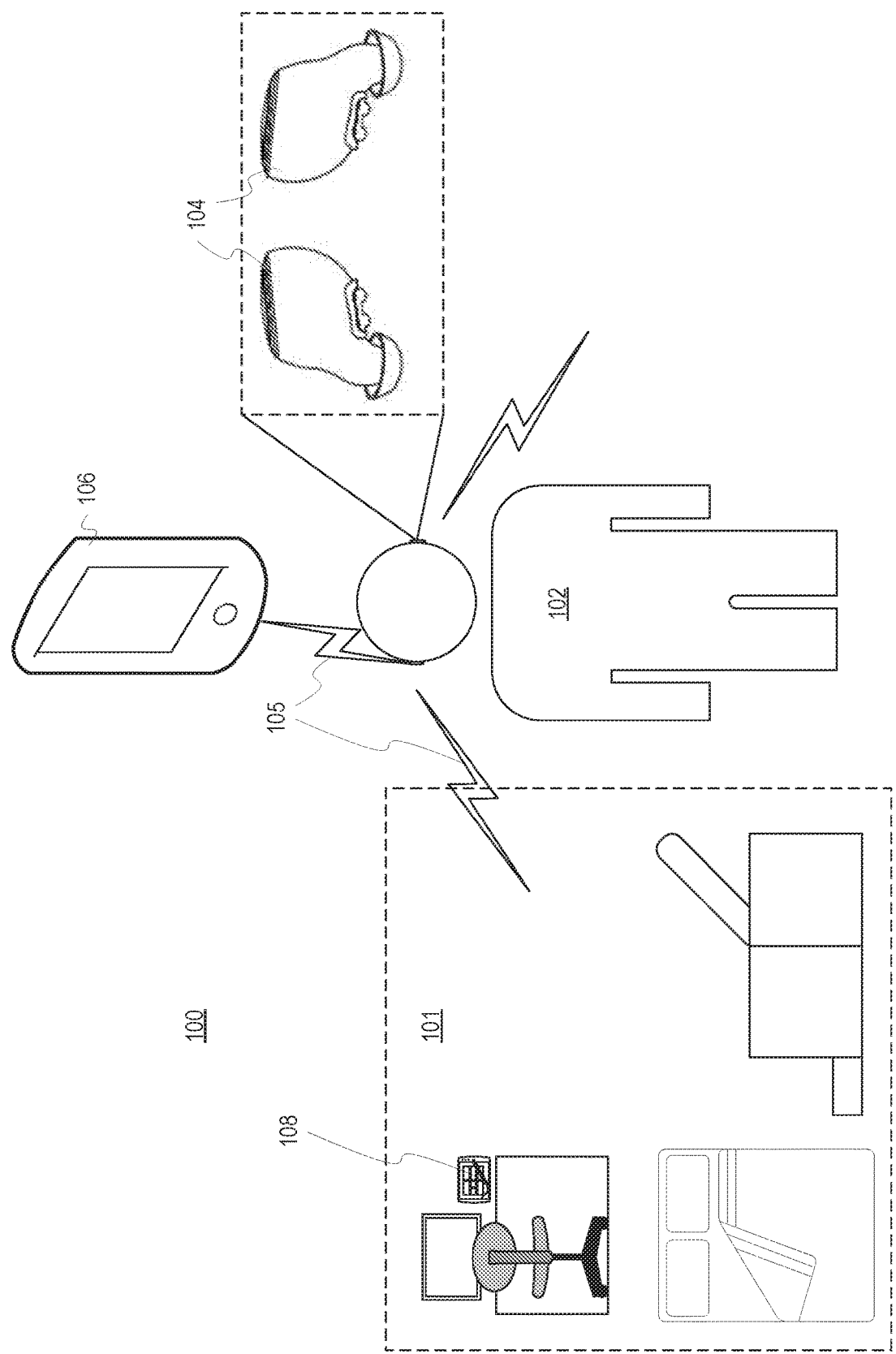
FIG. 1 is a pictorial representation of a communication system according to one aspect.

The present invention provides for generating and/or creating electronic health records (EHRs) from biometric data of wireless earpieces. The EHRs may be populated utilizing user, environmental, inertial, physiological, biological, device specific information, readings, or biometrics measured by the wireless earpieces. The EHRs may be stored locally by the wireless earpieces or the associated biometric information may be communicated to one or more additional wireless earpieces, computing, communications, or medical devices.

In one embodiment, the wireless earpieces may be part of a personal area network. The wireless earpieces may be utilized to control, communicate, manage, or interact with a number of other wearable devices, such as smart glasses, helmets, smart glass, watches or wrist bands, chest straps, implants, displays, clothing, or so forth. A personal area network is a network for data transmissions among devices, such as personal computing, communications, camera, vehicles, entertainment, and medical devices. The personal area network may utilize any number of wired, wireless, or hybrid configurations and may be stationary or dynamic. For example, the personal area network may utilize wireless network protocols, standards, or signals, such as INSTEON, IrDA, Wireless USB, Bluetooth, Z-Wave, ZigBee, Wi-Fi, ANT+, near field magnetic induction (NFMI), or other applicable radio frequency signals. In one embodiment, the personal area network may move with the user, such as between rooms in an apartment, business office, hospital, residence, or care facility.

The wireless earpieces may include any number of sensors for measuring user biometrics, such as pulse rate, blood oxygenation, temperature, calories expended, voice and audio output, and orientation (e.g., body, head, etc.). The sensors may also determine the user's location, position, velocity, impact levels, and so forth. The sensors may also receive user input and convert the user input into commands or selections made across the personal devices of the personal area network. For example, the user input detected by the wireless earpieces may include voice commands, head motions, finger taps, finger swipes, motions or gestures, or other user inputs sensed by the wireless earpieces. The user input may be determined and converted into commands that may be sent to one or more external devices, such as a tablet computer, smart phone, or so forth. The user input may be particularly important for users that may not be able to coherently speak or move enough to request help or assistance (e.g., reach a nurse call button, access a cell phone, etc.).

The wireless earpieces may also measure environmental or other data. For example, common environmental data may include temperature, barometric pressure, humidity, radiation, wind speed, altitude, exterior noise level, and so forth. The wireless earpieces may also receive measurements from third party devices that may include any number of sensors, such as smart watches, fitness trackers, pacemakers, cell phones, and so forth.

The EHRs allows the user to track and monitor any number of biometric, inertial, physiological and environmental measurements applicable to the user for personal use, including monitoring weight loss, tracking activity performance or monitoring health issues. The EHRs may be compiled over time or may represent a brief or limited sample of measurements or biometrics. The EHRs may represent minutes, hours, days, months, or even years of data. The user/wearer of the wireless earpieces may specify the data captured and integrated with the EHRs. In one embodiment, user preferences, settings, configurations, or parameters may be utilized to control how information and data is utilized to generate EHRs.

FIG. 1 is a pictorial representation of a communication system 100 in accordance with an illustrative embodiment. In one embodiment, the communication system 100 may represent a personal area network utilized by one or more users. The communication system 100 may also represent any number of systems, environments, or networks in which a user may utilize the described devices and components. For example, an environment 101 may be representative of a school, apartment, hospital, care facility, nursing home, residence, office building, or so forth. The environment 101 may be a location wherein the user 102 spends a substantial amount of time. The environment 101 may be a monitored environment or may be a location where the user is solely present.

In one embodiment, the communication system 100 may include a user 102 utilizing wireless earpieces 104 and communicating with a communications device 106. The wireless earpieces 104 may communicate with the communications device 106 through a wireless signal 105. The wireless earpieces 104 are shown as worn and separately from their positioning within the ears of the user 102 for purposes of visualization.

In one embodiment, the wireless earpieces 104 include a frame shaped to fit substantially within the ear of the user 102. The frame is a support structure that at least partially encloses and houses the electronic components of the wireless earpieces 104. The frame may include one or more sleeves configured to fit the inside of the ear of the user 102. The sleeves may have extremely tight tolerances to fit the size and shape of the ear of the user 102. In another embodiment, the sleeves may be custom built. In some applications, temporary adhesives or securing mechanisms (e.g., clamps, straps, extenders, etc.) may be utilized to ensure that the wireless earpieces 104 remain in the ears of the user 102 even during the most rigorous and physical activities. For example, the wireless earpieces 104 may be utilized in wet or humid environments, during sports, or so forth. The wireless earpieces 104 may be configured to play music or audio, receive and make phone calls, or other communications, activate and communicate with a digital assistant (e.g., Siri, Cortana, Alexa, smart assistant, etc.), determine ambient environmental conditions (e.g., temperature, altitude, location, speed, heading, etc.), read user biometrics (e.g., heart rate, motion, temperature, sleep, blood oxygenation, voice output, calories burned, forces experienced, etc.), and receive user input, feedback, or instructions.

In one embodiment, the user 102 is one of a group, team, or association of individuals participating in a common activity, event, game, or another happening. For example, the user 102 may represent one of a team coaches serving in a remote location. In one embodiment, the user 102 may remove the wireless earpieces 104 and place them in the ears of an athletic player to monitor the athletic players biometrics during practice to insure the biometric data is in satisfactory ranges. The biometrics from the user 102 or an athletic player as described in the example may be utilized to generate EHRs. These records may be utilized for the good of the user 102 or individual wearing the wireless earpieces 104.

In another embodiment, the user 102 may represent one individual of a team working jointly on a project, event, or operation. The user 102 may be able to communicate with one other users directly or indirectly utilizing the wireless earpieces 104. The communications system 100 may include any number of networks, repeaters, or extenders for extending the range and accessibility of the wireless earpieces 104.

The communications device 106 may receive biometric, inertial, biological, physiological, or environmental information for the user 102 enabling a single person or group too monitor the status and condition of the user 102. In other embodiments, the biometric data acquired for the user 102 for the corresponding wireless earpieces 104 may be sent remotely to any number of devices or systems. For example, the data may be archived in one or more remote servers and databases as an EHR for subsequent retrieval through a cloud network and interface. The EHRs may then be used for analysis, diagnosis, treatment formulation, real-time monitoring, and so forth. The information reported by the wireless earpieces 104 may be sent to a designated caregiver, relatives of each of the user 102, or other designated contacts. For example, a potentially dangerous impact detected by the wireless earpieces 104 for the user 102 may be reported to a caregiver utilizing the communications device 106.

The wireless earpieces 104 may be utilized for monitoring, diagnosis, early detection, and treatment of the user 102 based on an injury (e.g., head strike, hit, crash, accident, fall, etc.) or other detected health event (e.g., overheating, hypothermia, heart attack, stroke, seizure, asthma attack, electrocution, etc.). The wireless earpieces 104 may also detect a particular sound pattern or audio, such as a user groaning, screaming, or other audio event that may be associated with physical distress, a potential injury, or health event. The wireless earpieces 104 may include a library stored within their respective memories including one or more thresholds, values, user profiles, or data, for determining whether the user may be experiencing an injury or health event. In one embodiment, the user profile may specify the age, gender, weight, height, ethnicity, health conditions, activity level, and so forth.

The devices of the communication system 100 may include any number of devices, components, or so forth that may communicate with each other directly or indirectly through a wireless (or wired) connection, signal, or link, such as the wireless signals 105. The communications system 100 may be a network and may include any number of network components and devices, such as routers, servers, signal extenders, intelligent network devices, computing devices, or so forth. In one embodiment, the network of the communications system 100 represents a personal area network as previously disclosed. Communications, such as the wireless signals 105, within the communication system 100 may occur through the network or may occur directly between devices, such as the wireless earpieces 104 and the communications device 106 (e.g., direct communication of the wireless signal 105) or between the wireless earpieces 102 and the logging device 108 (indirect communication through a Wi-Fi network utilizing the wireless signal 105). In one embodiment, the communications system 100 may communicate with or include a wireless network, such as a Wi-Fi, cellular (e.g., 3G, 4G, 5G, PCS, GSM, etc.), Bluetooth, or other radio frequency network. The communications system 100 may also communicate with any number of hard wired networks, such as local area networks, coaxial networks, fiber-optic networks, or so forth. Communications within the communication system 100 may be operated by one or more users, service providers, or network providers.

As noted, both the wireless earpieces 104 as well as wearable or implantable devices utilized by the user 102 may include a number of sensors including touch sensors, optical sensors, pulse oximeters, microphones, accelerometers, gyroscopes, global positioning chips, and so forth for detecting the biometrics, motion, location, and activities of the user. The information may be utilized to coordinate the audio, video, text, and graphical information presented to the user 102 (as well as the communications device 106) by the respective wireless earpieces 104. In one embodiment, the user 102 may program the wireless earpieces 104 to perform specific activities in response to a specific biometric reading, user motion, command or audio signal, or other action. For examples, the user 102 may configure the wireless earpieces 104 (directly or indirectly through a user interface of a computing device communicating with the wireless earpieces 104) to send a concussion alert in response to sensing forces above a specified level applied to the head of the user 102.

Any number of user and environmental conditions may be utilized to generate alerts or other communications. The alerts may also be played audibly to the user 102. For example, the user may be played an alert indicating "you may be dehydrated, consider drinking water and taking a break", or "you just experience a significant impact, are you injured?" These same informational alerts may be communicated as text or audio to the wireless device 106 and/or the logging device 108. The wireless earpieces 104 as well as the communications device 106 may include logic for automatically communicating an alert in response to events, such as the user's 102, pulse stopping or slowing significantly (e.g., tracking sleep or rest patterns). Thus, the communication system 100 may be adapted to the needs and desires of the user 102.

In one embodiment, the communications device 106 may utilize short-range or long-range wireless communications to communicate with the wireless earpieces 104 through the wireless signal 105 or devices of the communications system 100 through the wireless signal 105. For example, the communications device 106 may include a Bluetooth, and cellular transceiver within the embedded logical components. For example, the wireless signal 106 may be a Bluetooth, Wi-Fi, NFMI, Zigbee, Ant+, or other short range wireless communication.

The communications device 106 may represent any number of wireless or wired electronic communications or computing devices, such as smart phones, laptops, desktop computers, control systems, tablets, displays, gaming devices, music players, personal digital assistants, vehicle systems, or so forth. The logging device 108 may represent any number of monitoring devices, such as personal computers (utilizing any number of monitoring applications), sleep analysis machines, athletic training devices, heart rate monitors, electrocardiogram machines, stress systems, diagnostic ultrasounds, pumps, lasers, diagnostic medical equipment, medical imaging, equipment, physical therapy machines, and so forth.

The communications device 106 and logging device 108 may communicate with the wireless earpieces 104 utilizing any number of wireless connections, standards, or protocols (e.g., near field communications, Bluetooth, Wi-Fi, wireless Ethernet, etc.). For example, the communications device 106 may be a touch screen cellular phone that communicates with the wireless earpieces 104 utilizing Bluetooth communications. The communications device 106 may implement and utilize any number of operating systems, kernels, instructions, or applications that may make use of the sensor data or user input received from the wireless earpieces 104. For example, the communications device 106 may represent any number of Android, iOS, Windows, open platforms, or other systems. Similarly, the communications device 106, the logging device 108, or the wireless earpieces 104 may include a number of applications that utilize the user input, biometric data, inertial data, physiological data, biological data, environmental data and other feedback from the wireless earpieces 104 to generate, edit, and display applicable information and data from electronic records, control the applications, play audible or tactile alerts, or make other selections. For example, biometric information (including, high, low, average, or other values) may be processed by the wireless earpieces 104, the communications device 106, or the logging device 108 to display experienced forces, heart rate, blood oxygenation, altitude, speed, distance traveled, calories burned, or other applicable information.

In one embodiment, the wireless device 106 may include any number of input components and sensors (e.g., similar to those described with regard to the wireless earpieces 104) that may be utilized to augment the input and sensor readings of the wireless earpieces 104. For example, a microphone of the wireless device 106 may determine an amount and type of ambient noise. The noise may be analyzed and utilized to filter the sensor readings made by the wireless earpieces 104 to maximize the accuracy and relevance of the sensor measurements of the wireless earpieces 104. For example, the wireless earpieces 104 may adjust the microphone sensitivity or filter out background noise based on measurements performed by the communications device 106. Filtering, tuning, and adaptation for the sensor measurements may be made for signal noise, electronic noise, or acoustic noise, all of which are applicable in the communication system 100. Sensor measurements made by either the wireless earpieces 104 or communications device 106 may be communicated with one another in the communication system 100. As noted, the communications device 106 is representative of any number of personal computing, communications, exercise, medical, or entertainment devices that may communicate with the wireless earpieces 104.

With respect to the wireless earpieces 104, sensor measurements or user input may refer to measurements made by one or both wireless earpieces 104 in a set. For example, the right wireless earpieces 104 may determine that the user may have experienced a concussive event even though the event was not detected by the left wireless earpiece 104. The wireless earpieces 104 may also switch back and forth between sensors of the left and right wireless earpieces 104 in response to varying noise, errors, or more accurate signals for both of the wireless earpieces 104. As a result, the clearest sensor signal may be utilized at any given time. In one embodiment, the wireless earpieces 104 may switch sensor measurements in response to the sensor measurements exceeding or dropping below a specified threshold. In one embodiment, the wireless earpieces 104 may be split between multiple users to monitor their condition simultaneously.

The user 102 may also have any number of wearable or implantable medical devices that may communicate with the wireless earpieces 104, wireless device 106, or the logging device 108. In one embodiment, the range of a wearable or implantable device may be sufficient to be read by the wireless earpieces 104, but insufficient to communicate with the wireless device 106 or the logging device 108. As a result, the wireless earpieces may temporarily or permanently store information as well as relaying biometric data from the wearable or implantable devices to generate and update electronic records.

The user 102 may be wearing or carrying any number of sensor-enabled devices, such as heart rate monitors, pacemakers, smart glasses, smart watches or bracelets (e.g., Apple watch, Fitbit, etc.), or other sensory devices that may be worn, attached to, or integrated with the user 102. The data and information from the external sensor devices may be communicated to the wireless earpieces 104. In another embodiment, the data and information from the external sensor devices may be utilized to perform additional processing of the information sent from the wireless earpieces 104 to the communications device 106 and/or logging device 108.

The sensors of the wireless earpieces 104 may be positioned at enantiomeric locations. For example, a number of colored light emitting diodes may be positioned to provide variable data and information, such as heart rate, respiratory rate, and so forth. The data gathered by the LED arrays may be sampled and used alone or in aggregate with other sensors. As a result, sensor readings may be enhanced and strengthened with additional data.

In another embodiment, the wireless earpieces 104 may represent or communicate with other wireless devices that may be ingested or implanted into a user. For example, the described electronics may be endoscopic pills, pacemakers, tracking devices, contact lenses, oral implants, bone implants, artificial organs, or so forth.

Figure 2:
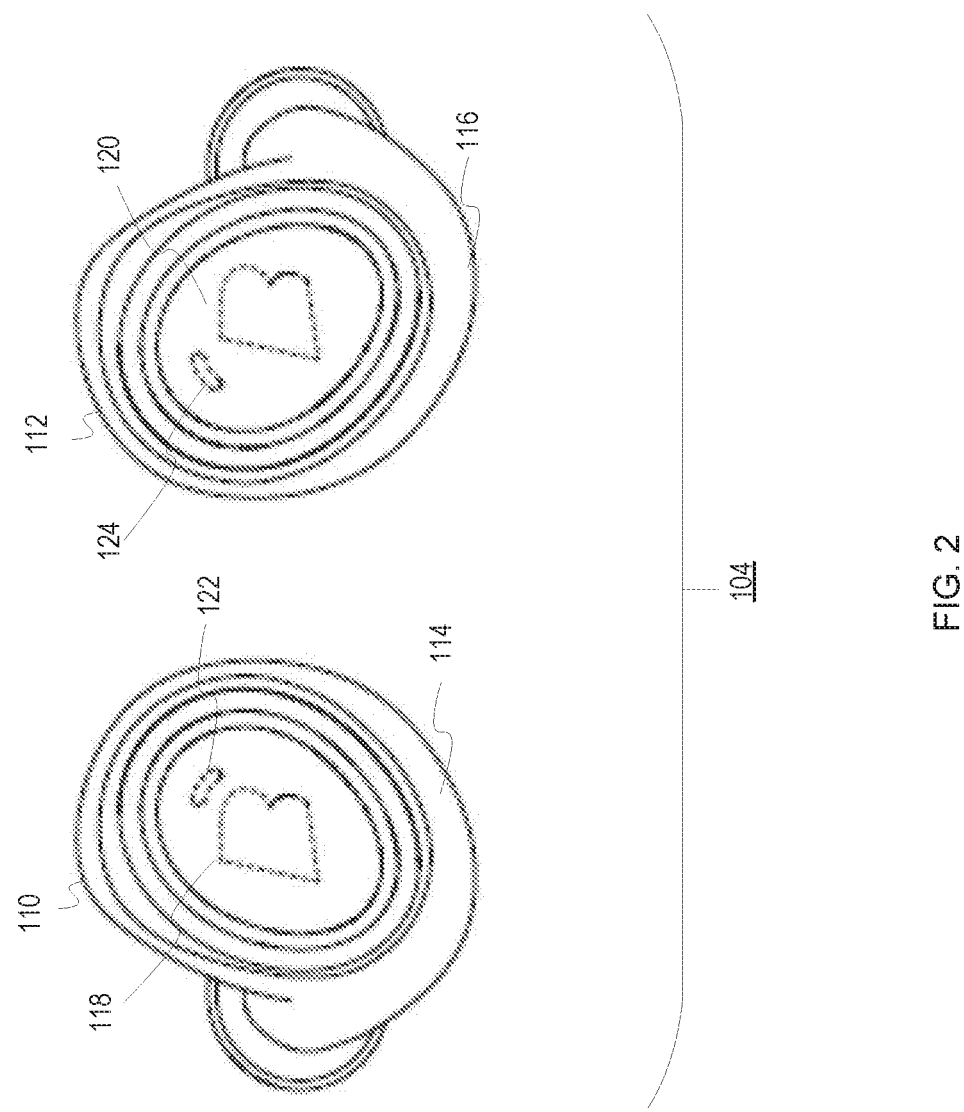
FIG. 2 is a pictorial representation of the wireless earpieces of the communications system of FIG. 1.

FIG. 2 is a pictorial representation of the wireless earpieces of the communications system of FIG. 1 in accordance with an illustrative embodiment. FIG. 2 illustrates one example of a wearable device in the form of a set of wireless earpieces 104 including a left wireless earpiece 110 and a right wireless earpiece 112. Each of the wireless earpieces 110, 112 has a housing 114, 116 which may be in the form of a protective shell, frame or casing and may be an in-the-ear earpiece housing. A left infrared through ultraviolet spectrometer 118 and right infrared through ultraviolet spectrometer 120 is also shown. Air microphones 122, 124 are also shown. Note that the air microphones 122, 124 are outward facing such that the air microphones 122, 124 may capture ambient environmental sound. It is to be understood that any number of microphones may be utilized in the illustrative embodiments.

Figure 3:
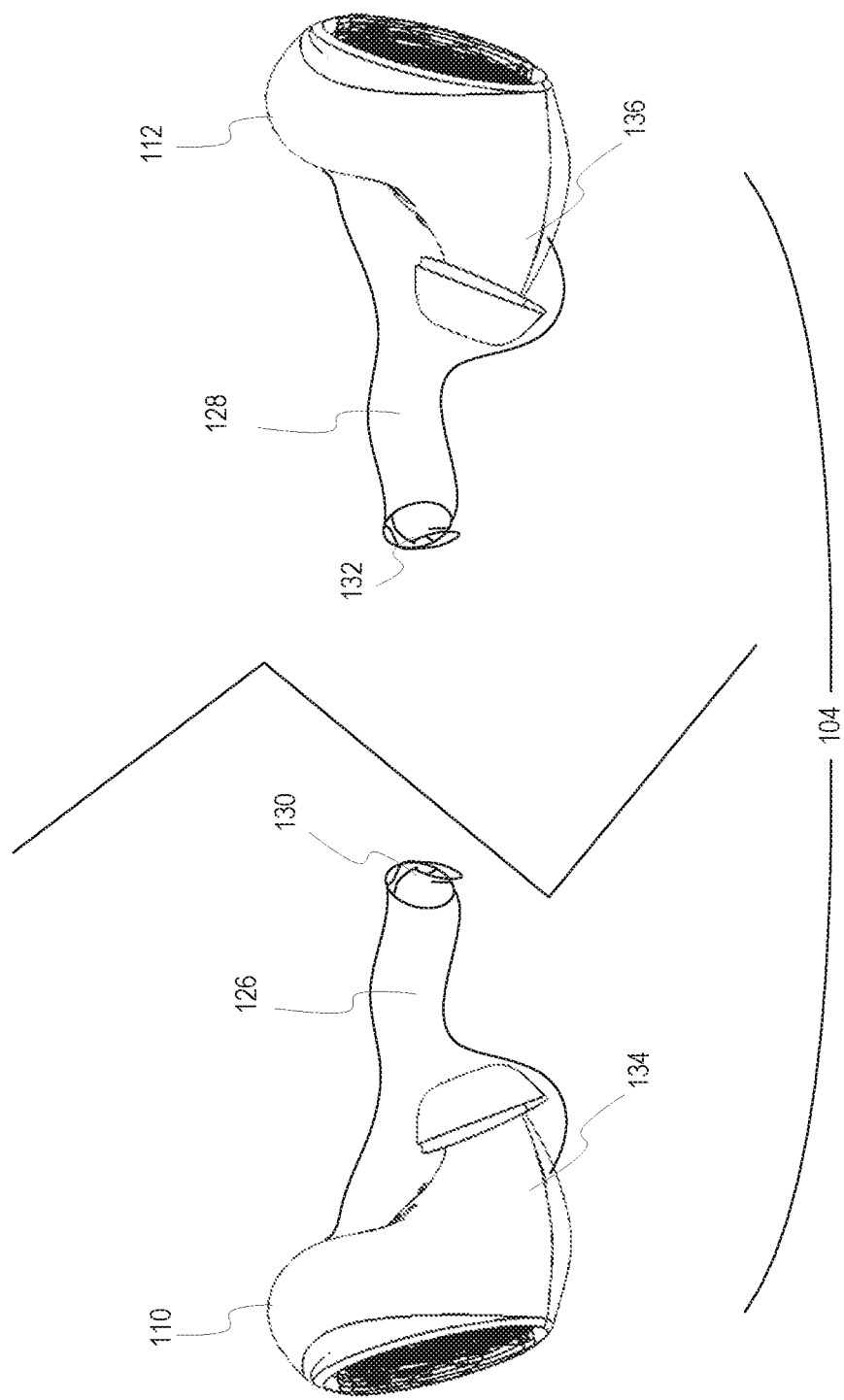
FIG. 3 illustrates a pair of wireless earpieces positioned within external auditory canals of a user.

FIG. 3 is a pictorial representation of the wireless earpieces of the communications system of FIG. 1. FIG. 3 illustrates wireless earpieces 110, 112 positioned within an ear of an individual or user when worn. The wireless earpieces 110, 112 each fit at least partially into external auditory canals 126, 128 of the user. A tympanic membrane 130, 132 is shown at the end of the external auditory canal 126, 128. Note that given the placement of each earpiece 110, 112 at least partially within the external auditory canal, one or more speakers of each earpiece 110, 112 is in very close proximity to the tympanic membrane 130, 132. Given the nature of ear canal earpieces, the ability to spatially localize the sound origin within a three-dimensional environment is heightened. This allows the user to experience the programming from different points of view, or alternatively, to focus on a particular position within the three-dimensional sound sphere. Through the use of appropriate algorithms, the user is able to select a position within the sound sphere for increased immersive effect. Alternatively, instead of selecting the position within the sound sphere, the programming may drive this selection.

The wireless earpieces 110, 112 further include any number of internal microphones, such as ear-bone microphones 134, 136. The ear-bone microphones 134, 136 may represent ear-bone or bone conduction microphones. The ear-bone microphones 134, 136 may sense vibrations, waves, or sound communicated through the bones and tissue of the user's body (e.g., skull). The ear-bone microphones 134, 136 and the external microphones previously described may work together to create an accurate sound profile.

Figure 4:
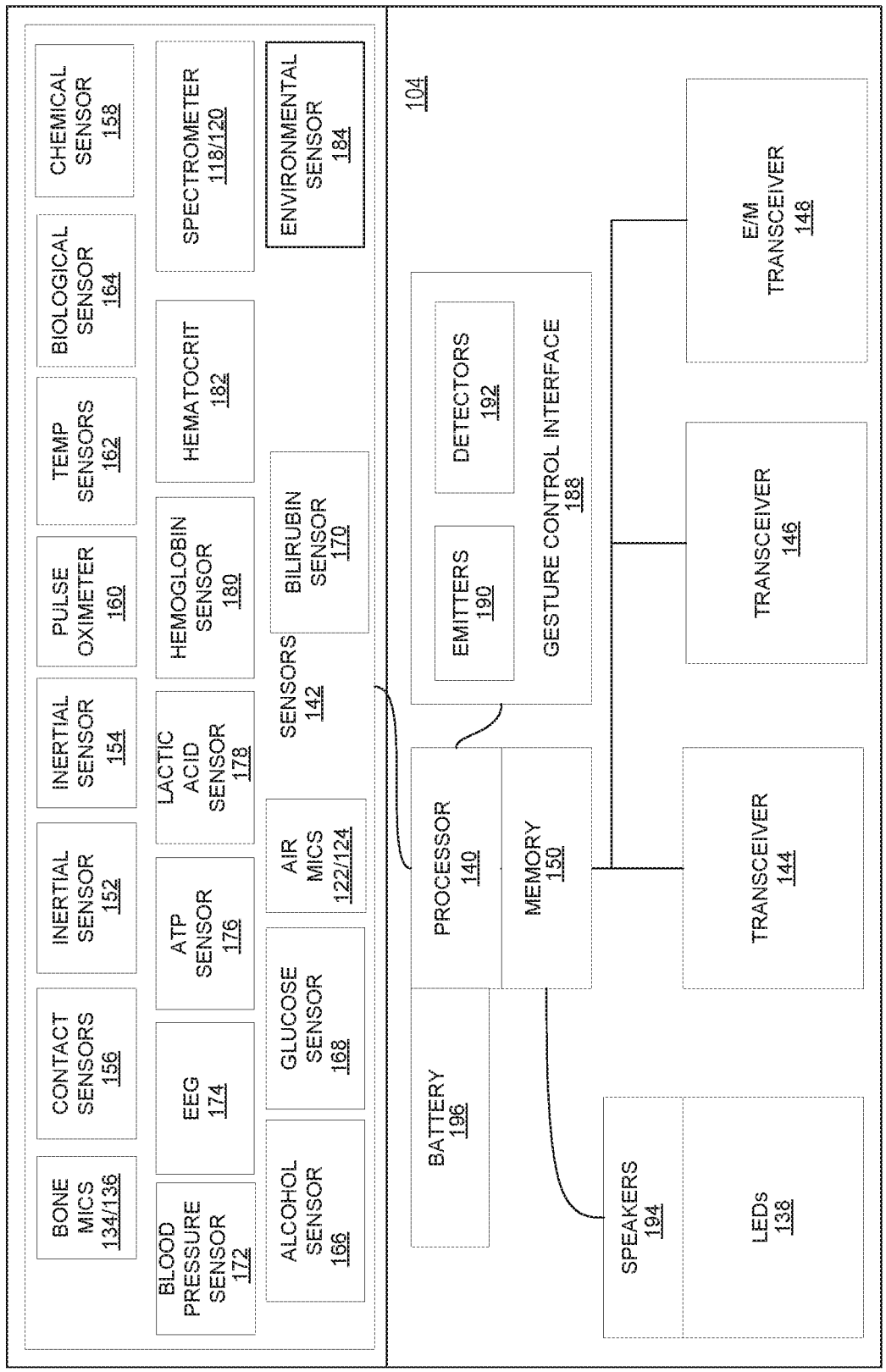
FIG. 4 is a block diagram of wireless earpieces.

FIG. 4 is a block diagram of wireless earpieces 104 in accordance with an illustrative embodiment. The description of the components, structure, functions, and other elements of the wireless earpieces 104 may refer to a left wireless earpiece, a right wireless earpiece, or both wireless earpieces 104 as a set or pair. All or a portion of the components shown for the wireless earpieces 104 may be included in each of the wireless earpieces. For example, some components may be included in the left wireless earpiece, but not the right wireless earpiece and vice versa. In another example, the wireless earpieces 104 may not include all the components described herein for increased space for batteries or so forth. The wireless earpieces may include one or more light emitting diodes (LEDs) 138 electrically connected to a processor 140 or other intelligent control system.

The processor 140 is the logic that controls the operation and functionality of the wireless earpieces 104. The processor 140 may include circuitry, chips, and other digital logic. The processor 140 may also include programs, scripts, and instructions that may be implemented to operate the various components of the wireless earpieces 104. The processor 140 may represent hardware, software, firmware, or any combination thereof. In one embodiment, the processor 140 may include one or more processors or logic engines. For example, the processor 140 may represent an application specific integrated circuit (ASIC) or field programmable gate array (FPGA). The processor 140 may utilize information from the sensors 142 to determine the biometric information, data, and readings of the user. The processor 140 may utilize this information and other criteria to inform the user of the biometrics (e.g., audibly, through an application of a connected device, tactilely, etc.) as well as communicate with other electronic devices wirelessly through the transceivers 144, 146, 148.

The processor 140 may also process user input to determine commands implemented by the wireless earpieces 110 or sent to the wireless earpieces 112 through the transceivers 144, 146, 148. Specific actions may be associated with biometric data thresholds. For example, the processor 140 may implement a macro allowing the user to associate biometric data as sensed by the sensors 142 with specified commands, alerts, and so forth. For example, if the temperature of the user is above or below high and low thresholds, an audible alert may be played to the user and a communication sent to an associated logging, monitoring, tracking, or medical device for communication to one or more coaches, parents, guardians, administrators, medical professionals, and so forth.

A memory 150 is a hardware element, device, or recording media configured to store data or instructions for subsequent retrieval or access at a later time. The memory 150 may represent static or dynamic memory. The memory 150 may include a hard disk, random access memory, cache, removable media drive, mass storage, or configuration suitable as storage for data, instructions, and information. In one embodiment, the memory 150 and the processor 150 may be integrated. The memory may use any type of volatile or non-volatile storage techniques and mediums. The memory 150 may store information related to the status of a user, wireless earpieces 104, interconnected electronic device, and other peripherals, such as a wireless device, smart glasses, smart watch, smart case for the wireless earpieces 104, wearable device, and so forth. In one embodiment, the memory 150 may display instructions, programs, drivers, or an operating system for controlling the user interface including one or more LEDs or other light emitting components, speakers, tactile generators (e.g., vibrator), and so forth. The memory 150 may also store the thresholds, conditions, biometric data (e.g., biometric and data library) associated with biometric events, inertial data, biological data, physiological data, or environmental data.

The processor 140 may also be electrically connected to one or more sensors 142. In one embodiment, the sensors 142 may include inertial sensors 152, 154 or other sensors that measure acceleration, angular rates of change, velocity, and so forth. For example, each inertial sensor 152, 154 may include an accelerometer, a gyro sensor or gyrometer, a magnetometer, a potentiometer, or other type of inertial sensor.

The sensors 142 may also include one or more contact sensors 156, one or more bone conduction microphones 134/136, one or more air conduction microphones 122/124, one or more chemical sensors 158, a pulse oximeter 160, a temperature sensor 162, or other physiological or biological sensors 164. Further examples of physiological or biological sensors 164 include an alcohol sensor 166, glucose sensor 168, or bilirubin sensor 170. Other examples of physiological or biological sensors 164 may also be included in the wireless earpieces 104. These may include a blood pressure sensor 172, an electroencephalogram (EEG) 174, an Adenosine Triphosphate (ATP) sensor 176, a lactic acid sensor 178, a hemoglobin sensor 180, a hematocrit sensor 182, or other biological or chemical sensor. The sensors may also include environmental sensors 184. These may include temperature sensors, barometric pressure sensors, humidity sensors, radition sensors, wind speed sensors, altitude sensors, exterior noise level sensors, and so forth.

A spectrometer 118/120 is also shown. The spectrometer 118/120 may be an infrared (IR) through ultraviolet (UV) spectrometer although it is contemplated that any number of wavelengths in the infrared, visible, or ultraviolet spectrums may be detected (e.g., X-ray, gamma, millimeter waves, microwaves, radio, etc.). In one embodiment, the spectrometer 118/120 is adapted to measure environmental wavelengths for analysis and recommendations, and thus, may be located or positioned on or at the external facing side of the wireless earpieces 104.

A gesture control interface 188 is also operatively connected to the processor 140. The gesture control interface 188 may include one or more emitters 190 and one or more detectors 192 for sensing user gestures. The emitters 190 may be of any number of types including infrared LEDs, lasers, and visible light.

The wireless earpieces may also include a number of transceivers 144, 146, 148. The transceivers 144, 146, 148 are components including both a transmitter and receiver which may be combined and share common circuitry on a single housing. The transceivers 144, 146, 148 may communicate utilizing Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. The transceivers 144, 146, 148 may also be a hybrid transceiver that supports a number of different communications. For example, the transceiver 144, 146, 148 may communicate with other electronic devices or other systems utilizing wired interfaces (e.g., wires, traces, etc.), NFC or Bluetooth communications. For example, a transceiver 144 may allow for induction transmissions such as through near field magnetic induction (NFMI).

Another transceiver 146 may utilize any number of short-range communications signals, standards or protocols (e.g., Bluetooth, BLE, UWB, etc.), or other form of radio communication may also be operatively connected to the processor 140. The transceiver 146 may be utilized to communicate with any number of communications, computing, or network devices, systems, equipment, or components. The transceiver 146 may also include one or more antennas for sending and receiving signals.

In one embodiment, the transceiver 148 may be a magnetic induction electric conduction electromagnetic (E/M) transceiver or other type of electromagnetic field receiver or magnetic induction transceiver that is also operatively connected to the processor 140 to link the processor 140 to the electromagnetic field of the user. For example, the use of the transceiver 148 allows the device to link electromagnetically into a personal area network, body area network, or other device.

In operation, the processor 140 may be configured to convey different information using one or more of the LEDs 138 based on context or mode of operation of the device. The various sensors 142, the processor 140, and other electronic components may be located on the printed circuit board of the device. One or more speakers 194 may also be operatively connected to the processor 404.

The wireless earpieces 104 may include a battery 196 that powers the various components to perform the processes, steps, and functions herein described. The battery 196 is one or more power storage devices configured to power the wireless earpieces 104. In other embodiments, the battery 196 may represent a fuel cell, thermal electric generator, piezo electric charger, solar charger, ultra-capacitor, or other existing or developing power storage technologies.

Although the wireless earpieces 104 shown includes numerous different types of sensors and features, it is to be understood that each wireless earpiece need only include a basic subset of this functionality. It is further contemplated that sensed data may be used in various ways depending upon the type of data being sensed and the particular application(s) of the earpieces.

As shown, the wireless earpieces 104 may be wirelessly linked to any number of wireless or computing devices (including other wireless earpieces) utilizing the transceivers 144, 146, 148. Data, user input, feedback, and commands may be received from either the wireless earpieces 104 or the computing device for implementation on either of the devices of the wireless earpieces 104 (or other externally connected devices). As previously noted, the wireless earpieces 104 may be referred to or described herein as a pair (wireless earpieces) or singularly (wireless earpiece). The description may also refer to components and functionality of each of the wireless earpieces 104 collectively or individually.

In some embodiments, linked or interconnected devices may act as a logging tool for receiving information, data, or measurements made by the wireless earpieces 104. For example, a linked computing device may download data from the wireless earpieces 104 in real-time. As a result, the computing device may be utilized to store, display, and synchronize data for the wireless earpieces 104. For example, the computing device may display pulse rate, blood oxygenation, blood pressure, temperature, and so forth as measured by the wireless earpieces 104. In this example, the computing device may be configured to receive and display alerts that indicate a specific health event or condition has been met. For example, if the forces applied to the sensors 138 (e.g., accelerometers) indicates that the user may have experienced a concussion or serious trauma, the wireless earpieces 104 may generate and send a message to the computing device. The wireless earpieces 104 may have any number of electrical configurations, shapes, and colors and may include various circuitry, connections, and other components.

The components of the wireless earpieces 104 may be electrically connected utilizing any number of wires, contact points, leads, busses, wireless interfaces, or so forth. In addition, the wireless earpieces 104 may include any number of computing and communications components, devices or elements which may include busses, motherboards, circuits, chips, sensors, ports, interfaces, cards, converters, adapters, connections, transceivers, displays, antennas, and other similar components.

The wireless earpieces 104 may also include physical interfaces (not shown) for connecting the wireless earpieces with other electronic devices, components, or systems, such as a smart case or wireless device. The physical interfaces may include any number of contacts, pins, arms, or connectors for electrically interfacing with the contacts or other interface components of external devices or other charging or synchronization devices. For example, the physical interface may be a micro USB port. In one embodiment, the physical interface is a magnetic interface that automatically couples to contacts or an interface of the computing device. In another embodiment, the physical interface may include a wireless inductor for charging the wireless earpieces 104 without a physical connection to a charging device.

As originally packaged, the wireless earpieces 104 may include peripheral devices such as charging cords, power adapters, inductive charging adapters, solar cells, batteries, lanyards, additional light arrays, speakers, smart case covers, transceivers (e.g., Wi-Fi, cellular, etc.), or so forth.

Figure 5:
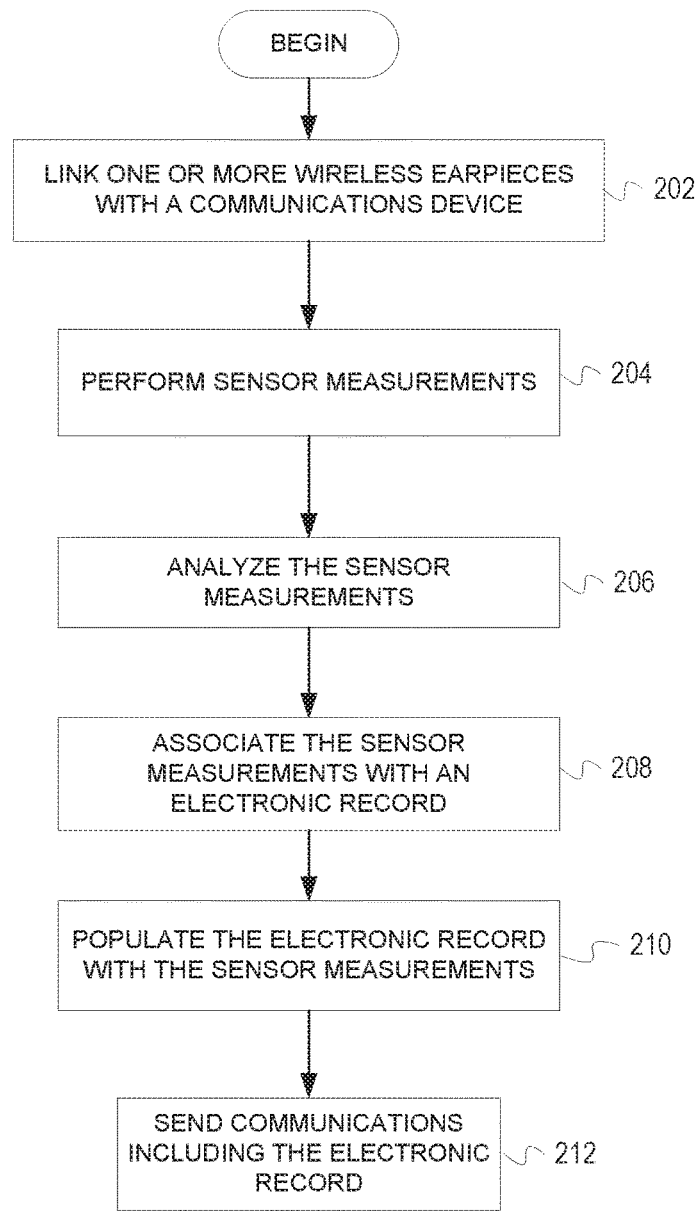
FIG. 5 is a flowchart of a process for populating electronic records utilizing wireless earpieces.

FIG. 5 is a flowchart of a process for populating EHRs utilizing wireless earpieces in accordance with an illustrative embodiment. The process of FIG. 5 may be implemented by one or more wireless earpieces. The wireless earpieces may be in communication with wearable devices, medical implants, monitors, and/or any number of communication or computing devices referred to in FIG. 5 as a communication device for purposes of simplicity. The method of FIG. 5 may be performed by a set of wireless earpieces for each of the wireless earpieces individually. The wireless earpieces may also communicate directly or indirectly with the communication device through a personal area network or other network. The process of FIG. 5 may be performed utilizing logic of the wireless earpieces including hardware, software, firmware, or a combination thereof. In one embodiment, an application may be utilized to generate and populate an EHR based on sensor measurements associated with a user. In one embodiment, wireless earpieces with different sensor arrays may be utilized by different users, providers, and for differing circumstances of the user. As a result, the read sensor measurements may vary for personal use, athletic activities/facilities, office workspaces, and so forth.

In one embodiment, the process of FIG. 5 may begin by linking one or more wireless earpieces with a communications device (step 202). The wireless earpieces may be linked with the communications device utilizing any number of communications, standards, or protocols. For example, the devices may be linked by a Bluetooth connection. The process may require that the devices be paired utilizing an identifier, such as a passcode, password, serial number, voice identifier, radio frequency, or so forth. The wireless earpieces may be linked with the communications device and any number of other devices directly or through a network, such as a personal area network. The wireless earpieces and the communication device may be linked, connected, or paired, such that any time they are within range or approximate each other, they may begin communicating.

Next, the wireless earpieces perform sensor measurements (step 204). The sensor measurements may include performing any number of biometric, inertial, physiological, biological and environmental measurements applicable to the user. The measurements may be performed utilizing a predefined sampling rate (e.g., 1 second, 100 milliseconds, once a minute, etc.). The sensor measurements may also be triggered in response to detected events or thresholds, such as change in user orientation or position (e.g., change from vertical to horizontal position), changes in velocity (e.g., extreme starts, stops, accelerations, etc.), high forces (e.g., impacts, jolts, etc.), or detected events from other sensors worn by the user. The sensor measurements may also be performed in response to any number of settings, instructions, requests, feedback, programs, or so forth. The settings may be specified by the user, an athletic coach/trainer, a medical professional, a health monitoring program, a guardian, or other authorized user. For example, an athletic coach associated with the user may utilize a graphical user interface available through the communication's device (or other associated device) to set the times, conditions, events, circumstances, stimuli, biometrics, location, user orientation or other factors utilized to perform the sensor measurements. The sensor measurements may be performed specifically to generate or update an associated electronic record.

Next, the wireless earpieces analyze the sensor measurements (step 206). The sensor measurements may be processed or otherwise evaluated by the wireless earpieces. For example, one or more processors of the wireless earpieces may process the incoming sensor data measurements. For example, the analysis may include determining or verifying one of a potential number of users utilizing the wireless earpieces. To further illustrate, an EHR may only be generated and updated for a child previously associated with the wireless earpieces (e.g., a user profile has been established). The analysis may also include processing raw data from the wireless earpieces to generate values, data, or other input that may be integrated with the electronic record. The sensor measurements are processed for subsequent analysis, determinations, or decisions, implemented by the wireless earpieces.

The analysis or processing of the sensor measurements (step 206) may also provide for generating a summary of the sensor measurements or an analysis of the sensor measurements. The summary may take on one of numerous types of forms. For example, the summary may include low and high sensor readings for a particular time period. The summary may include an average sensor reading over a particular time period. The summary may include sensor data from environmental sensors as well as biometric sensors in order to assist one in interpreting the biometric data. For example, data from the environmental sensors may include lighting conditions, ambient sound levels, ambient temperature, location, or other information. The summary may also indicate the number of sensor readings, or other information used to describe the data set whether quantitatively or qualitatively. The ability to have both environmental data and biometric data provides additional context for the electronic health record. In one aspect, both the underlying data as well as the summary is including within an electronic health record so that additional analysis may be performed with the best available data if needed, but making basic information such as that included in the summary readily available and easily accessible as not all electronic health record systems may be configured to interpret it.

Next, the wireless earpieces associate the sensor measurements and the summary of the sensor measurements (if present) with an EHR (step 208). The sensor measurements of step 208 may represent the analyzed or processed measurements as performed during step 206 (e.g., values, data points, information, etc.). In one embodiment, the wireless earpieces may associate the identified user with an associated EHR. Any number of names, identifiers, profiles or other information included in or integrated with the wireless earpieces or the EHR may be utilized to ensure that the sensor measurements are associated with the corresponding EHR. It is to be further understood the wireless earpieces may store identifying information about the user which may be used in generating the electronic health record. The identifying information may include a patient identifier or universal patient identifier, a name of the patient/user, a date of birth of the patient/user, a social security number or other government issued identifier for the patient/user or combinations of identifying information so that certainty regarding the identity of the user is provided. It is to be understood that more than one piece of identifying information may be present. It is contemplated that in some instances the wireless earpieces may have more than one user and in other cases the wireless earpieces may have a single user.

Next, the wireless earpieces populate the electronic record with the sensor measurements (step 210). The EHR may be populated or updated utilizing real-time measurements, at specified intervals, utilizing queued/saved data, or so forth. In one embodiment, an electronic record may be generated for the user. For example, during any of the steps of FIG. 5, an EHR may be created for a specified user. A template, form, database, web/cloud interface, or other specified information may be utilized to create the blank electronic record for the user. In another embodiment, the EHR may already exist for the user, and thus, the electronic record may be further populated with data during step 210. For example, heart rate, temperature, blood pressure, and motion of the user may be associated with particular fields, parameters, or settings and may specify a date/time of the sensor measurements. Additional data may also be associated with the EHR, such as position, orientation, location, additional users proximate or in communication with the user, and other applicable information. In one embodiment, the EHR may be populated as an automated process. In another embodiment, the EHR may be updated in response to one or more biometric thresholds associated with the user being exceeded. The wireless earpieces may populate all of the EHR or only data fields or portions of the EHR associated with the sensor measurements.

Next, the wireless earpieces send communications including the EHR to at least the communications device (step 212). The wireless earpieces may send the EHR to any number of specified or default users, devices, systems, equipment, components, or so forth. For example, the EHR may be communicated to a wireless device, such as a smart phone. The smart phone may then relay the EHR to a server, monitoring system, web/cloud interface, or so forth. As a result, an athletic coach associated with the user may be able to view the most recent data, information, values, and updates of the electronic record as associated biometric data, inertial data, physiological data, biological data, or environmental data is captured by the wireless earpieces. In another example, the EHR may be sent directly to a tablet of an athletic coach. The EHR may be displayed utilizing an application that presents the EHR visually (e.g., graphs, charts, thresholds, trends, averages, data points, etc.), mathematically, audibly, or so forth.

Figure 6:
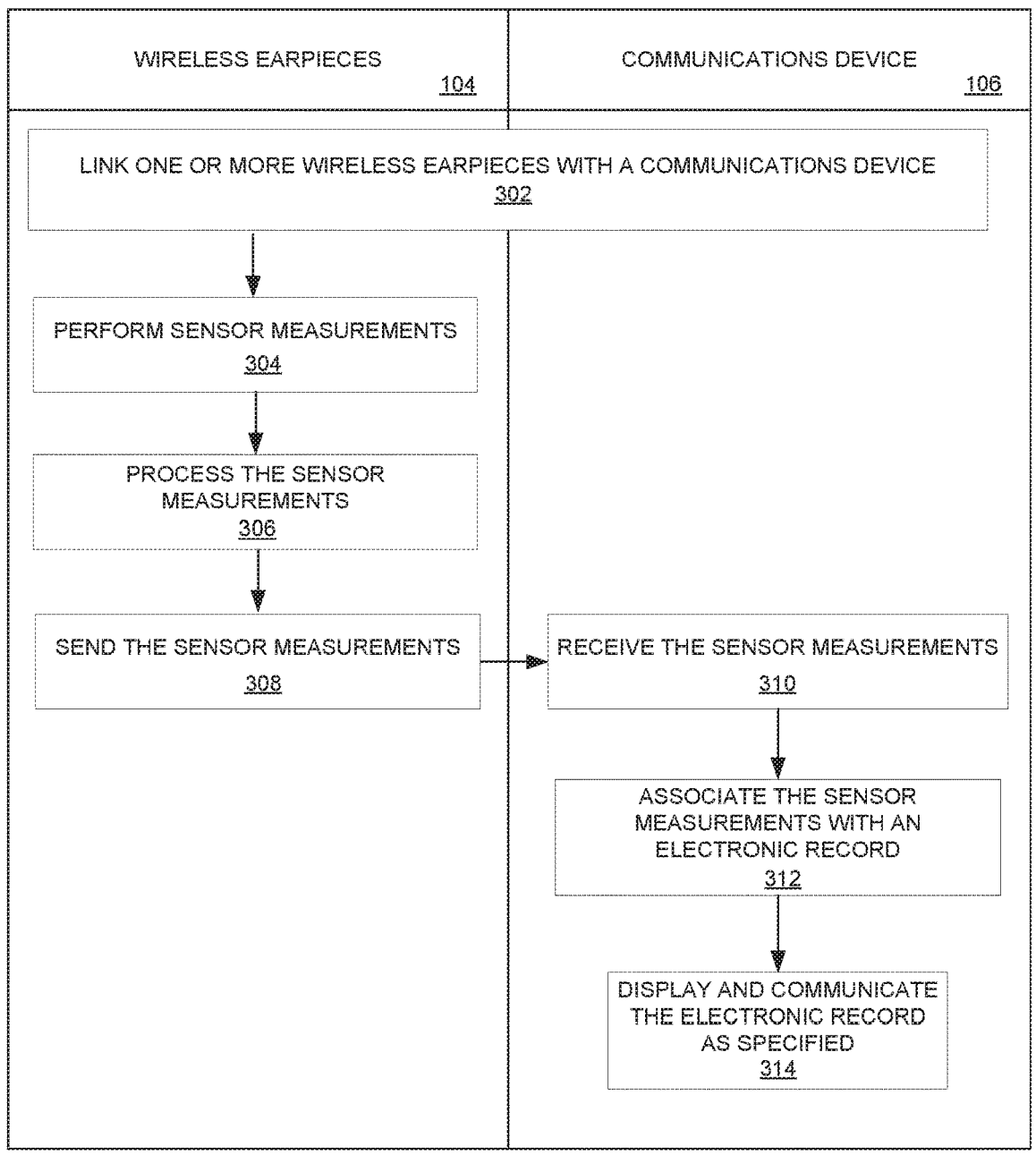
FIG. 6 is a flowchart of a process for populating electronic records between devices utilizing wireless earpieces.

FIG. 6 is a flowchart of a process for populating EHRs between devices utilizing wireless earpieces in accordance with an illustrative embodiment. The process of FIGS. 6 and 7 may be implemented by wireless earpieces 104 and a communications device 106. Many of the steps and description associated with FIG. 5 are similarly applicable to FIGS. 6 and 7.

In one embodiment, the process may begin by linking the wireless earpieces 104 with the communications device 106 (step 302). As previously noted, any number of standards, protocols, or signals may be utilized to connect, associate, or link the wireless earpieces 104 with the communications device 106.

Next, the wireless earpieces 104 perform sensor measurements (step 304). In addition, to the wireless earpieces 104, sensor measurements may be taken by the communications device 106, implantable devices, wearable devices (e.g., smart or biometric watches, wristbands, headbands, jewelry, etc.).

Next, the wireless earpieces 104 process the sensor measurements (step 306). During step 306, the wireless earpieces 104 may process the raw data into a format that may be utilized by the communications device 106. For example, the wireless earpieces 104 may convert the raw data into data, values, or information that may be more easily inserted into EHR. In one example, the processing may include associating a time stamp with the biometrics read by the wireless earpieces 104. As a result, an athletic coach reading the EHR may have a time and date associated with biometric data of interest. In other embodiments, the wireless earpieces 104 may further associated information, such as location, orientation, position, user detected activity, user voice output (e.g., speech recordings, voice-to-text translations, stress levels, amplitude, frequency, etc.). The information shared by the wireless earpieces 104 is approved by the user or a guardian of the user. The wireless earpieces 104 may also process the sensor measurements into a format that is more easily communicated to the communications device 104 which may include packetization, frame generation, signal processing and preparation, data encryption, digital-to-analog conversion, data compression, modulation, coding, and so forth.

Next, the wireless earpieces 104 send the sensor measurements to the communications device 106 (step 308). The sensor measurements may be communicated to the communication device 106 as well as any number of other devices, simultaneously, sequentially, concurrently, or so forth.

Next, the communications device 106 receive the sensor measurements (step 310). An established link, connection, or signals may be utilized to communicate the sensor measurements during step 310. In one embodiment, the communications are performed directly utilizing a signal, such as Bluetooth, Wi-Fi, or so forth.

Next, communications device 106 associates the sensor measurements with an electronic record (step 312). In one embodiment, the wireless earpieces 104 may have been associated with a particular user. For example, device identifiers for the wireless earpieces 104 may be associated with an EHR to ensure that information is properly recorded, authenticated, stored, and subsequently accessed. In one embodiment, user biometrics (e.g., voice authentication, skin conductivity, fingerprint analysis, etc.) may be utilized by the wireless earpieces 104 to associate the user with the wireless earpieces 104 and the sensor measurements with an associated EHR.

Next, the communications device 106 displays and communicates the EHR as specified (step 314). The EHR may be communicated to users and devices designated by the user, authorized guardians, authorized athletic coaches, authorized medical professionals, or authorized physical therapists and so forth.

In additional embodiments and steps, the wireless earpieces or the communications device 106 may determine whether sensor measurement thresholds are exceeded. The wireless earpieces may include any number of thresholds, including, high and low thresholds for measurements, such as forces experienced by the user, acceleration, temperature, pulse rate, blood oxygenation, blood pressure, and so forth.

In response to determining the sensor measurement thresholds are exceeded, the wireless earpieces may send communications regarding the user's condition to the communications device for recording in the EHR. For example, the communications may be an alert, status update, warning, or other similar information. In one embodiment, the communication may be an alert indicating that the user may have experienced a concussion. Likewise, the communication may indicate that the user's temperature has exceeded a threshold and may be experiencing overheating. The information from the wireless earpieces may be particularly valuable for users, such as athletes or athletic coaches. For example, the wireless earpieces may be utilized while training to ensure that a patient's heart rate does not spike. The communications device 106 may be monitored by athletic trainers/coaches, medical professionals, guardians, health services groups, parents, or other monitoring groups to ensure the safety of the user. Additional sensors may be utilized as needed to monitor the user and verify measurements before one or more actions are performed. For example, additional measurements may be taken by a smart watch, or chest strap worn by the user. In another example, a pacemaker of the user may provide additional data regarding pulse, heart rhythm, and other applicable or measured information.

Figure 7:
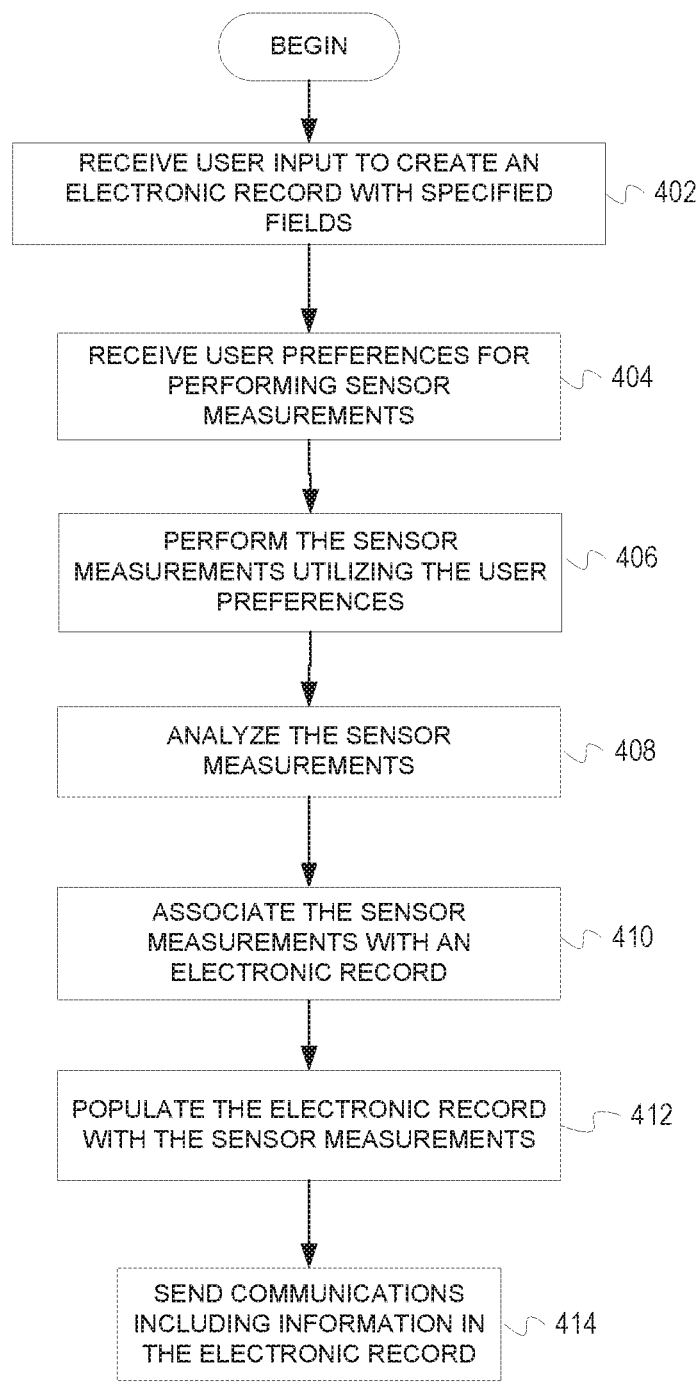
FIG. 7 is a flowchart of another process for populating electronic records between devices utilizing wireless earpieces.

FIG. 7 is a flowchart of another process for populating EHRs between devices utilizing wireless earpieces in accordance with an illustrative embodiment. The process of FIG. 7 may begin by receiving user input to create an electronic record with specified fields (step 402). In one embodiment, the fields may correspond to biometric data, user data, biological data, physiological data, environmental data, or other information or data that may be read, acquired, measured, or retrieved by the wireless earpieces or associated electronic devices (e.g., cell phone, smart watch, heart rate monitor, pedometer, etc.). The EHRs may be created utilizing the wireless earpieces, such as through verbal commands, or through an application, interface, program, script, macro, or other instructions that may be executed by a smart phone, tablet, home computer, laptop, or other computing or communications device associated with the wireless earpieces.

Next, the wireless earpieces receive user preferences for performing sensor measurements (step 404). The user preferences may specify what sensor measurements are made, how they are made, and when the sensor measurements are made. For example, the user preferences may specify that the user's vitals are taken once every 30 seconds and include temperature, pulse rate, blood pressure, and blood oxygenation. In another example, the user preferences may specify that cadence, distance travelled, and average heart rate are tracked anytime a biking feature is activated. The user preferences may specify any number of measurements that are performed with respect to the user, environment, wireless earpiece performance and communication, wireless device performance, and so forth.

Next, the wireless earpieces perform the sensor measurements utilizing the user preferences (step 406).

Next, the wireless earpieces analyze the sensor measurements (step 408). The wireless earpieces may perform all of the analysis or may prepare and format the data to be offloaded to an associated electronic device, such as a cell phone, laptop, or medical diagnostic device, to perform the full or more detailed analysis.

Next, the wireless earpieces associate the sensor measurements with an EHR (step 410). During step 410, the specified fields of the EHR are filled. The EHRs may be updated over time with new measurements.

Next, the wireless earpieces populate the EHR with the sensor measurements (step 412). The EHR may be populated according the user input and user preferences. In one embodiment, the user input of step 402 may be all or a portion of the user preferences of step 404.

Next, the wireless earpieces send communications including information in the EHR (step 414). In one embodiment, the EHR may be communicated according to user preferences. For example, the EHR may be audibly communicated to a wearer of the wireless earpieces as well as communicated to a smart phone linked via Bluetooth/apps with the wireless earpieces. All or portions of the EHR (e.g., fields, text, data, etc.) may be communicated during step 414.

The illustrative embodiments provide a system, method, personal area network, and wireless earpieces for communicating an EHR including sensor measurements to one or more externally connected devices. The sensor measurements are utilized to update EHRs, send communications, updates, alerts, or other information relative to the condition of the user as well as the user's environment. In one embodiment, the sensor measurements may be updated on the wireless earpieces or sent to a remote device to update the EHR. The illustrative embodiments may be utilized to monitor, protect, diagnose, treat, and train the user based on one or more sensor measurements that are made.

Computer program code for carrying out operations of the embodiments may be written in any combination of one or more programming languages, including an object-oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method for populating an electronic health record by wireless earpieces including a first wireless earpiece and a second wireless earpiece, the first wireless earpiece having a first earpiece housing and the second wireless earpiece having a second earpiece housing, the method comprising steps of:
receiving user input through the wireless earpieces to create the electronic health record wherein the user input specifies fields within the electronic health record and wherein the user input includes identifying information of to "a user of the wireless earpieces;
creating the electronic health record at the wireless earpieces, the electronic health record including the fields specified by the user input;
receiving a selection of user preferences at the wireless earpieces using one or more sensors of the wireless earpieces, wherein at least one of the one or more sensors is disposed within the first earpiece housing of the wireless earpieces;
performing a set of sensor measurements at the wireless earpieces based on the user preferences using the one or more sensors of the wireless earpieces;
associating the set of sensor measurements with the user by a processor disposed within the first earpiece housing;
summarizing the set of sensor measurements using the processor disposed within the first earpiece housing to provide a sensor data summary;
populating the fields of the electronic health record using the set of sensor measurements, the sensor data summary, and the identifying information of the user, the populating the electronic health record performed using the processor disposed within the first earpiece housing;
translating a portion of the electronic health record into speech by the wireless earpieces;
outputting the translated portion of the electronic health record to the user by a speaker of the wireless earpieces; and
storing the populated electronic health record in a memory of one of the wireless earpieces, the memory operatively connected to the processor and disposed within the first earpiece housing.

2. The method of claim 1 wherein the identifying information of the user comprises at least two of a patient id, a name of the user, a date of birth of the user, and a social security number of the user.

3. The method of claim 2 wherein the sensor data summary comprises a time period for the sensor measurements, a high reading and a low reading for each type of sensor measurements.

4. The method of claim 1 wherein the one or more sensors include at least one environmental sensor and at least one biometric sensor and wherein the sensor measurements include both biometric data of the user from the at least one biometric sensor and environmental data of an environment associated with the user from the at least one environmental sensor and wherein the environmental data provides context for the biometric data.

5. The method of claim 4 wherein the biometric data comprises pulse data and inertial data.

6. The method of claim 1 wherein the one or more sensors include at least one biometric sensor disposed within the first earpiece housing, the set of sensor measurements include sensor measurements from the at least one biometric sensor within the first wireless earpiece, and the first wireless earpiece further comprises (a) a wireless transceiver disposed within the first earpiece housing and the processor is operatively connected to the at least one biometric sensor and the wireless transceiver, (b) at least one microphone operatively connected to the processor, and (c) an inertial sensor operatively connected to the processor, wherein the selection of user preferences is performed utilizing the inertial sensor of the first earpiece, wherein the memory is configured to store the populated electronic health record and the sensor data summary.

7. A method for populating an electronic health record utilizing wireless earpieces, comprising:
providing the wireless earpieces, the wireless earpieces including a first wireless earpiece and a second wireless earpiece;
identifying a user of the wireless earpieces by the wireless earpieces utilizing at least one sensor within a first earpiece housing for the first wireless earpiece;
receiving user input through the wireless earpieces to create the electronic health record by the wireless earpieces wherein the user input specifies a plurality of fields within the electronic health record to the wireless earpieces and wherein the plurality of fields includes identifying information of the user and a biometric data field;
creating the electronic health record by an intelligent control of the first wireless earpiece, the electronic health record including the plurality of fields within the electronic health record specified by the user input;
receiving a selection of user preferences at the wireless earpieces utilizing at least an inertial sensor disposed within the first earpiece housing;
performing sensor measurements of the user utilizing a plurality of sensors of the wireless earpieces wherein the plurality of sensors include at least one biometric sensor disposed within the first earpiece housing and at least one environmental sensor;
summarizing the sensor measurements by the intelligent control of the first wireless earpiece to store in the electronic health record;
populating the plurality of fields of the electronic health record with the sensor measurements and the summary of the sensor measurements, the populating the electronic health record performed using the intelligent control of the first wireless earpiece, the intelligent control disposed within the first earpiece housing;
translating the summary of the sensor measurements into speech by the wireless earpieces;
communicating the translated summary of the sensor measurements audibly to the user using a speaker of the wireless earpieces;
storing the populated electronic health record in a memory of the first wireless earpiece, the memory operatively connected to the intelligent control disposed within the first earpiece housing; and sending the electronic health record from the wireless earpieces to another device.

8. The method of claim 7 wherein the sensor measurements include biometric data sensed by the at least one biometric sensor disposed within the first earpiece housing, the selection of user preferences performed using the inertial sensor disposed within the first earpiece housing:

wherein the first earpiece further comprises a wireless transceiver disposed within the first earpiece housing for voice communications, the intelligent control disposed within the first earpiece housing is operatively connected to the at least one biometric sensor disposed within the first earpiece housing, the inertial sensor and the wireless transceiver are disposed within the first earpiece housing, at least one microphone is operatively connected to the intelligent control of the first earpiece, a near field magnetic induction transceiver of the first earpiece is operatively connected to the intelligent control of the first earpiece for communication with the second earpiece, the memory is configured to store the populated electronic health record;

wherein the second earpiece comprises at least one biometric sensor disposed within a second earpiece housing, an intelligent control of the second earpiece operatively connected to the at least one biometric sensor disposed within the second earpiece housing, at least one microphone of the second earpiece operatively connected to the intelligent control of the second earpiece, an inertial sensor of the second earpiece operatively connected to the intelligent control of the second earpiece, a near field magnetic induction transceiver of the second earpiece operatively connected to the intelligent control of the second earpiece for communication with the first earpiece, a memory of the second earpiece operatively connected to the intelligent control of the second earpiece.

9. The method of claim 7, wherein the sensor measurements include at least pulse, blood pressure, temperature, and user experienced forces.

10. The method of claim 7 wherein the summarizing of the sensor measurements includes at least a high value for the sensor measurements and a low value for the sensor measurements.

11. The method of claim 10 wherein the summarizing includes an average for the sensor measurements.

12. The method of claim 1 further comprising:

communicating the sensor data summary to the user of the wireless earpieces using a speaker disposed within the first earpiece housing and operatively connected to the processor.

13. The method of claim 6 wherein the electronic health record comprises a plurality of fields, wherein a first field of the plurality of fields comprises the identifying information of the user, a second field of the plurality of fields comprises biometric data sensed by the at least one biometric sensor disposed within the first earpiece housing, a third field of the plurality of fields comprises inertial data sensed by the inertial sensor of the first earpiece.

* * * * *

UNITED STATES PATENT AND TRADEMARK OFFICE
CERTIFICATE OF CORRECTION

PATENT NO. : 11,694,771 B2
APPLICATION NO. : 15/927851
DATED : July 4, 2023
INVENTOR(S) : Peter Vincent Boesen It is certified that error appears in the above-identified patent and that said Letters Patent is hereby corrected as shown below:

In the Claims

Column 19, Claim 1, Line 25 change "to "a user of the wireless earpieces" to --a user of the wireless earpieces--

Signed and Sealed this
Fifteenth Day of August, 2023

Katherine Kelly Vidal
*Director of the United States Patent and Trademark Office*